US010806326B2

(12) United States Patent
Arai

(10) Patent No.: US 10,806,326 B2
(45) Date of Patent: *Oct. 20, 2020

(54) METHOD FOR OBSERVING THE BRANCH PORTION OF THE HOLE AND METHOD FOR OPERATING THE ENDOSCOPE SYSTEM

(71) Applicant: OLYMPUS CORPORATION, Tokyo (JP)

(72) Inventor: Norimasa Arai, Tama (JP)

(73) Assignee: OLYMPUS CORPORATION, Tokyo (JP)

( * ) Notice: Subject to any disclaimer, the term of this patent is extended or adjusted under 35 U.S.C. 154(b) by 660 days.

This patent is subject to a terminal disclaimer.

(21) Appl. No.: 15/488,686

(22) Filed: Apr. 17, 2017

(65) Prior Publication Data

US 2018/0296071 A1 Oct. 18, 2018

(51) Int. Cl.
*A61B 1/233* (2006.01)
*A61B 1/005* (2006.01)
*A61B 1/00* (2006.01)

(52) U.S. Cl.
CPC ...... *A61B 1/00071* (2013.01); *A61B 1/00009* (2013.01); *A61B 1/00064* (2013.01); *A61B 1/233* (2013.01); *A61B 1/00043* (2013.01); *A61B 1/0051* (2013.01); *A61B 1/00114* (2013.01); *A61B 1/00135* (2013.01)

(58) Field of Classification Search
CPC .............. A61B 1/0008; A61B 1/00098; A61B 1/00133; A61B 1/00172; A61B 1/0051; A61B 1/233; A61B 1/00009; A61B 1/00043; A61B 1/00045; A61B 1/00135

USPC .................................................. 600/114, 115
See application file for complete search history.

(56) References Cited

U.S. PATENT DOCUMENTS

| | | | | |
|---|---|---|---|---|
| 5,807,239 A | * | 9/1998 | DiBernardo | A61B 1/00135 600/114 |
| 5,899,851 A | * | 5/1999 | Koninckx | A61B 1/05 348/E5.03 |
| 6,471,637 B1 | * | 10/2002 | Green | A61B 1/00045 600/109 |
| 6,855,107 B2 | * | 2/2005 | Avni | A61B 1/0005 600/114 |
| 8,221,308 B2 | * | 7/2012 | Noguchi | A61B 1/31 600/114 |
| 2005/0228230 A1 | * | 10/2005 | Schara | A61B 1/00045 600/171 |
| 2006/0084840 A1 | * | 4/2006 | Hoeg | A61B 1/00045 600/117 |

(Continued)

*Primary Examiner* — John P Leubecker
(74) *Attorney, Agent, or Firm* — Scully, Scott, Murphy & Presser, P.C.

(57) ABSTRACT

A method for observing the branch portion of the hole comprising, a step of pushing an obstacle in the hole with an elbow portion; a step of rotating a guide member around an axial direction so that a distal portion of the guide member faces the branch portion extending laterally to an extending direction of the hole; a step of projecting an endoscope from the distal portion and inserting into the branch portion, while confirming an image; and a step of rotating the image to match an up-and-down direction of the image recognized by a user with an up-and-down of a vertical direction, after the endoscope is inserted into the branch portion.

11 Claims, 16 Drawing Sheets

(56) References Cited

U.S. PATENT DOCUMENTS

| | | | |
|---|---|---|---|
| 2007/0167682 A1* | 7/2007 | Goldfarb | A61B 1/00135 600/114 |
| 2007/0250105 A1* | 10/2007 | Ressemann | A61B 17/12022 606/196 |
| 2007/0282305 A1* | 12/2007 | Goldfarb | A61B 1/0014 604/528 |
| 2008/0097154 A1 | 4/2008 | Makower et al. | |
| 2008/0159653 A1* | 7/2008 | Dunki-Jacobs | A61B 1/04 382/293 |
| 2008/0172033 A1* | 7/2008 | Keith | A61B 1/00154 604/506 |
| 2008/0262301 A1* | 10/2008 | Gibbons | A61B 1/00082 600/114 |
| 2009/0187098 A1 | 7/2009 | Makower et al. | |
| 2010/0125166 A1* | 5/2010 | Henzler | A61B 1/00177 600/109 |
| 2012/0078043 A1* | 3/2012 | Miyayashiki | A61B 1/00004 600/109 |
| 2013/0281778 A1* | 10/2013 | Suehara | A61B 1/233 600/104 |
| 2015/0005805 A1* | 1/2015 | Kesten | A61B 17/24 606/196 |
| 2016/0287054 A1* | 10/2016 | Fujitani | A61B 1/00078 |

\* cited by examiner

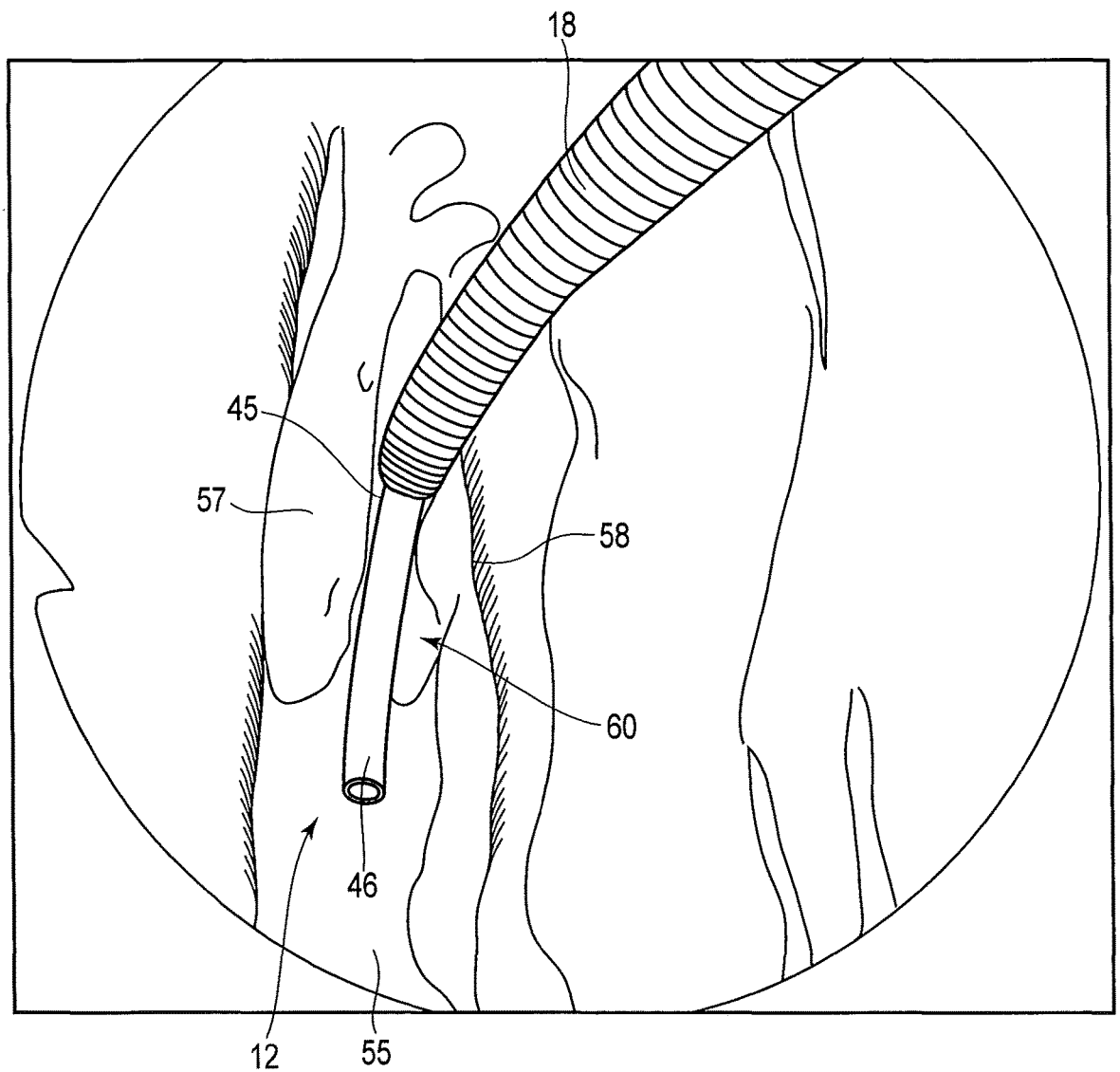
F I G. 4

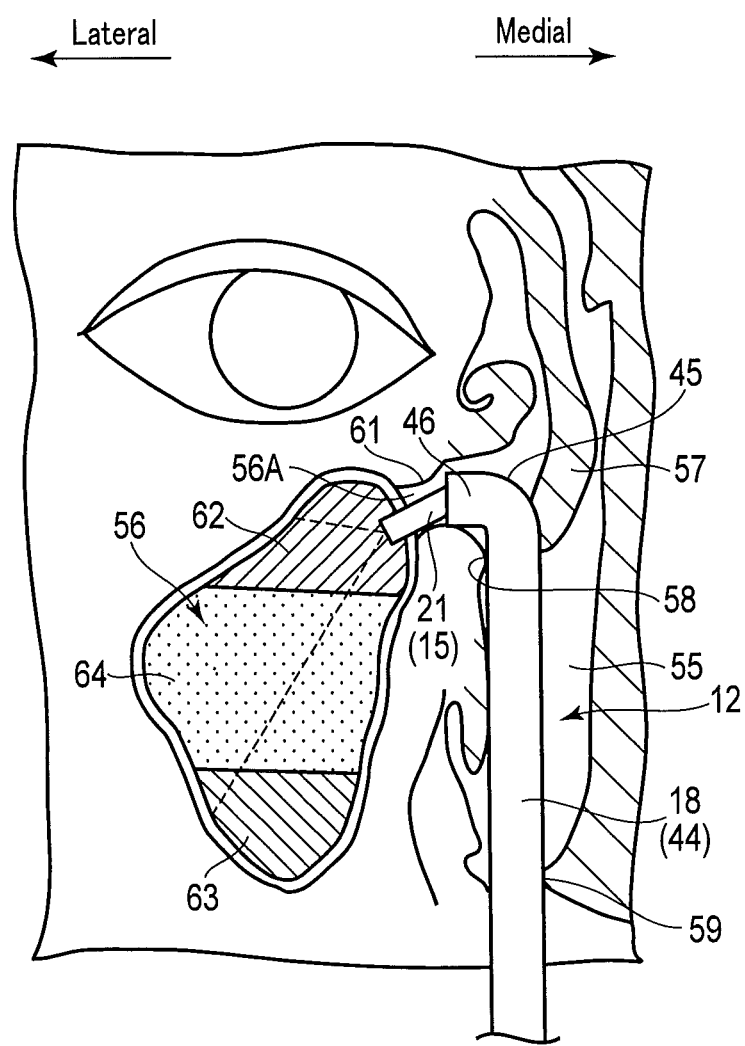
F I G. 11

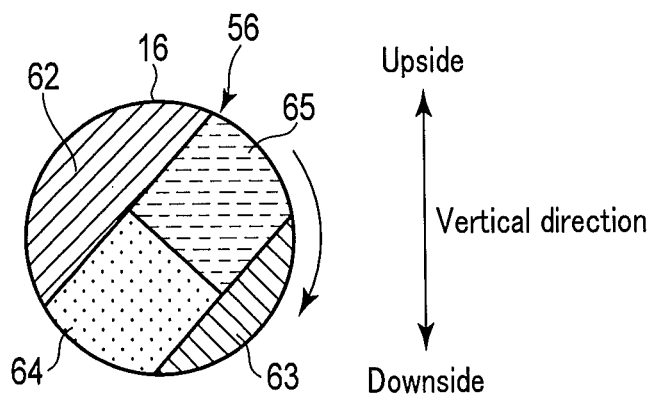
F I G. 13
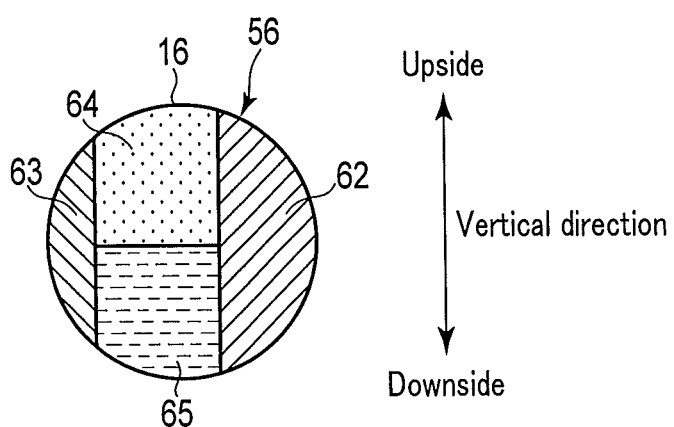
F I G. 14

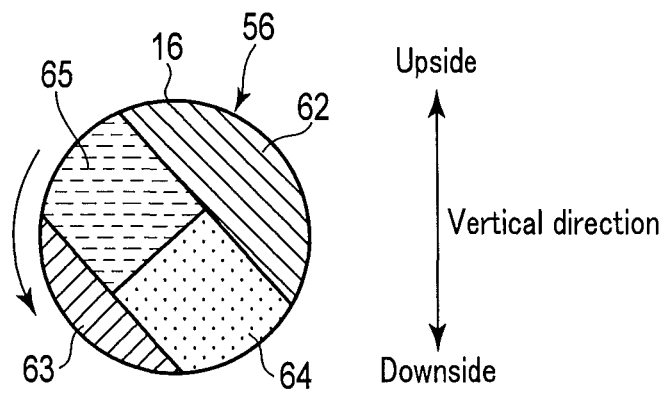
F I G. 17
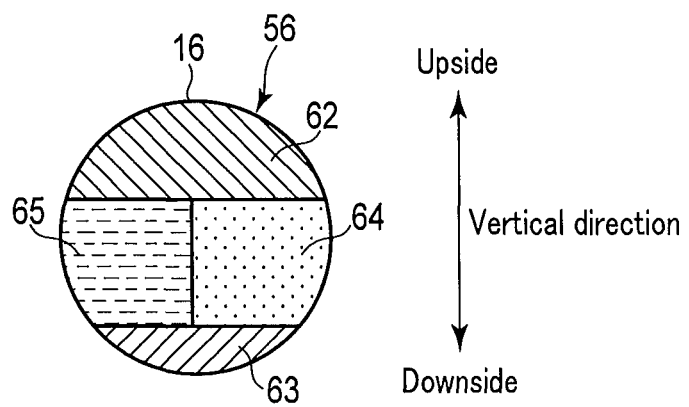
F I G. 18

METHOD FOR OBSERVING THE BRANCH PORTION OF THE HOLE AND METHOD FOR OPERATING THE ENDOSCOPE SYSTEM

BACKGROUND OF THE INVENTION

1. Field of the Invention

This invention relates to a method for observing a branch portion of a hole which enables visual recognition of the inside of the hole of an observation target, and a method for operating an endoscope system.

2. Description of the Related Art

For example, in US2008/0097154A1, there is disclosed a device which is useful for treatments of diseases of paranasal sinuses. As represented by this patent literature, a surgical procedure to be performed under an endoscope broadly spreads in the treatment of chronic sinusitis.

BRIEF SUMMARY OF THE INVENTION

A method for observing a branch portion of a hole which uses an endoscope system comprising a guide member having an elbow portion and a distal portion extending laterally from the elbow portion, an endoscope whose orientation is adjustable by the guide member, a controller which processes a signal acquired from the endoscope to generate an image, and a display which displays the image generated by the controller, the method for observing the branch portion of the hole comprising: a step of pushing an obstacle in the hole with the elbow portion; a step of rotating the guide member around an axial direction so that the distal portion faces the branch portion extending laterally to an extending direction of the hole; a step of projecting the endoscope from the distal portion and inserting into the branch portion, while confirming the image; and a step of rotating the image to match an up-and-down direction of the image recognized by a user with an up-and-down of a vertical direction, after the endoscope is inserted into the branch portion.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 4 is a perspective view showing a state just before inserting the guide pipe into a space between the obstacle (middle nasal concha) that is present in the hole (a nasal cavity) and the wall area defining the periphery of the hole in the endoscope system shown in FIG. 1;

FIG. 11 is a schematic view showing a state where the endoscope and the guide pipe are inserted into a hole (right nasal cavity) of a medical examinee in a recumbent posture and a branch portion (a paranasal sinus and right maxillary sinus) in a second example of the method for observing the branch portion of the hole (the method for operating the endoscope system);

FIG. 13 is a schematic view showing an image (an image of a state prior to rotation at an angle) obtained from the endoscope in the state shown in FIG. 11;

FIG. 14 is a schematic view showing an image after the image shown in FIG. 13 is rotated at the angle;

FIG. 17 is a schematic view showing an image (an image of a state prior to rotation at an angle) obtained from the endoscope in the state shown in FIG. 15;

FIG. 18 is a schematic view showing an image after the image shown in FIG. 17 is rotated at the angle;

DETAILED DESCRIPTION OF THE INVENTION

Embodiments

Hereinafter, there will be described embodiments of an endoscope system and a method for observing a branch portion of a hole which uses the endoscope system (a method for operating the endoscope system) with reference to FIG. 1 to FIG. 18.

Figure 1:
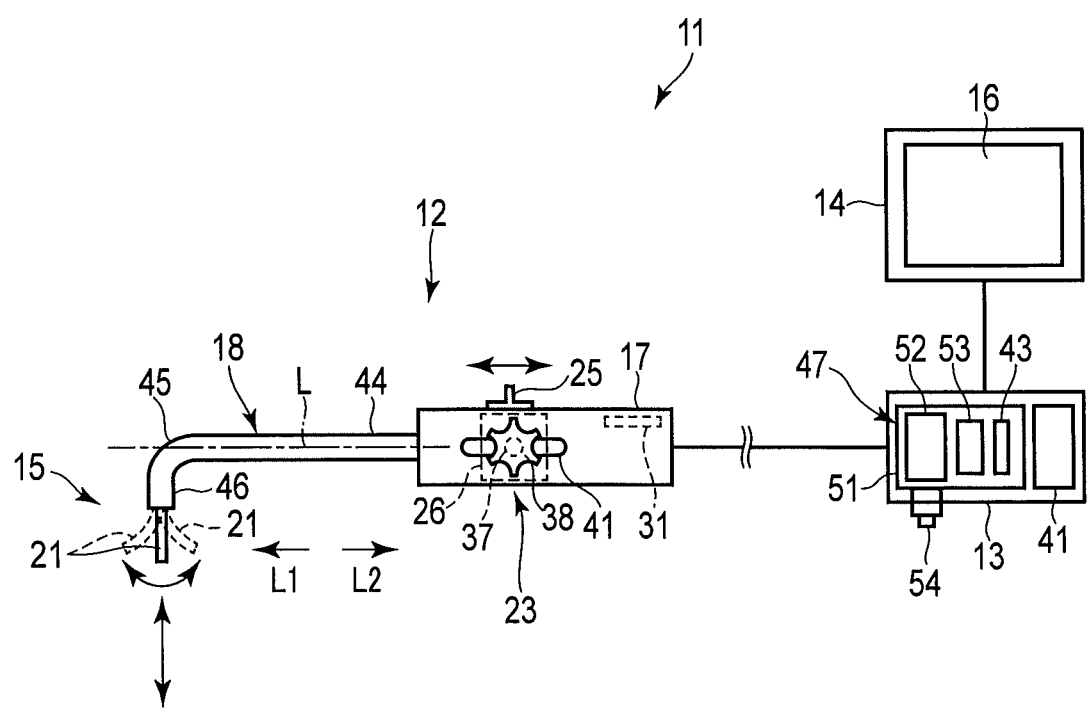
FIG. 1 is a schematic view showing an entire configuration of an endoscope system according to a first embodiment.

As shown in FIG. 1, an endoscope system 11 includes an insertion device 12 to be inserted into a nasal cavity, a paranasal sinus and the like and used, a controller 13 electrically connected to the insertion device 12 via an electric power line through which an electric power is to be supplied and via various signal lines, and a display 14 connected to the controller 13. The insertion device 12 is provided separately from the display 14 and the controller 13. The display 14 is constituted of a usual liquid crystal monitor and is capable of displaying an image 16 (an endoscopic image) acquired from an endoscope 15.

Figure 2:
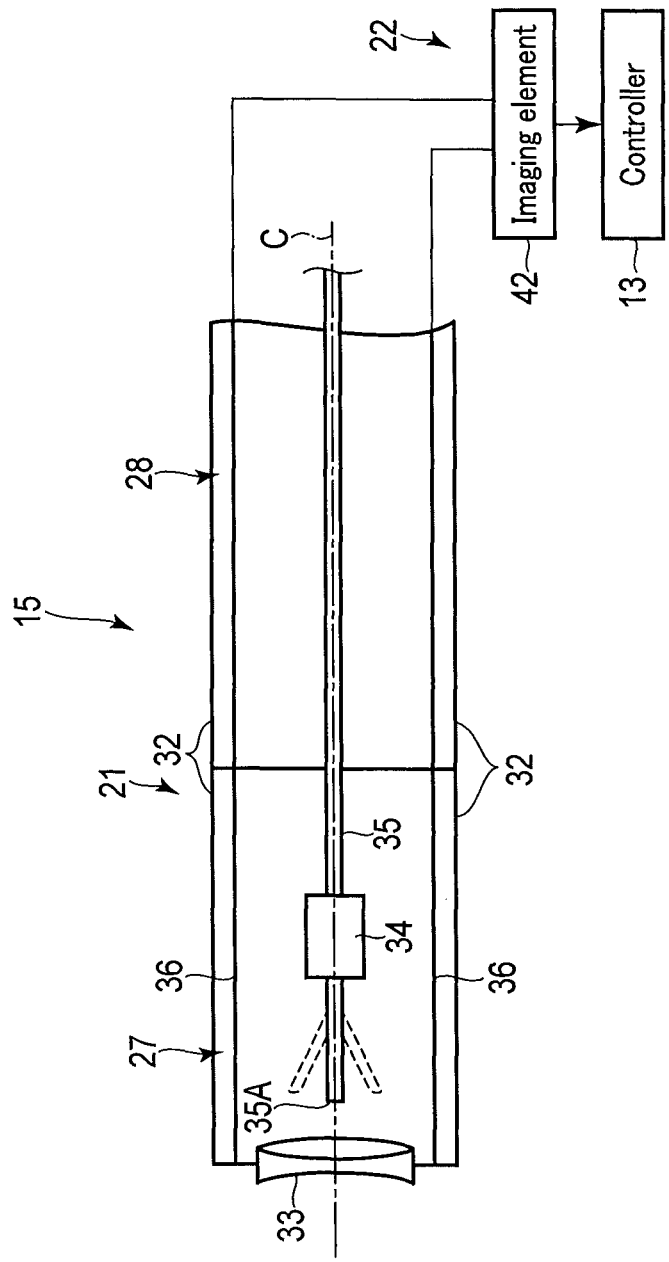
FIG. 2 is a side view showing, in a perspective manner, the vicinity of a distal end constituting portion of an endoscope insertion section of the endoscope system shown in FIG. 1.
Figure 6:
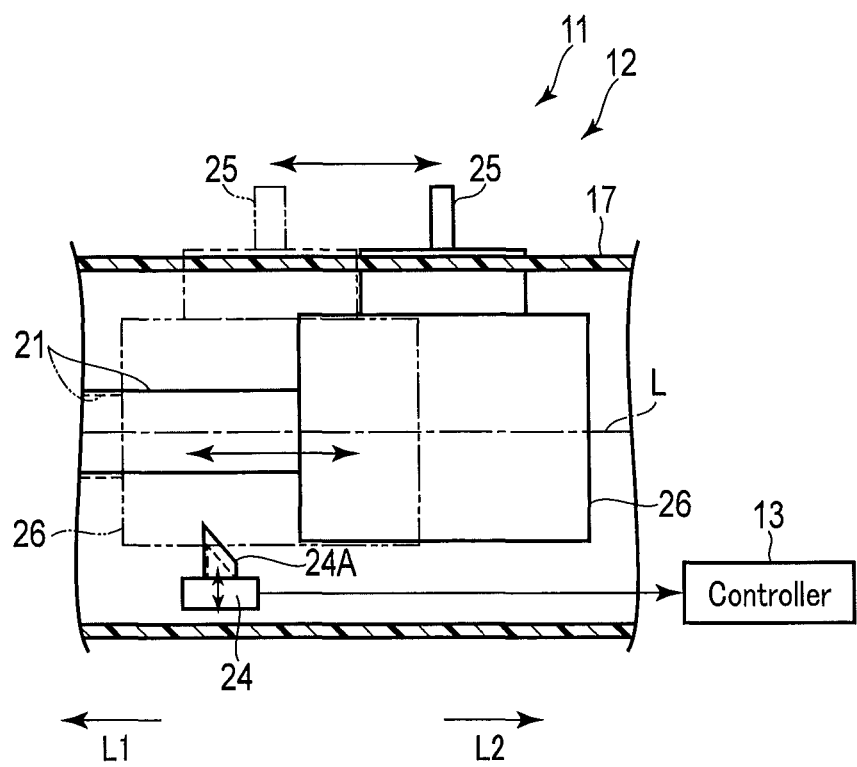
FIG. 6 is a sectional view showing a state where an advancing/retreating mechanism is operated, whereby a support unit moves to advance and retreat in a holding section.

As shown in FIG. 1 and FIG. 2, the insertion device 12 includes a holding section 17 constituting an outer shell, a tubular guide pipe 18 protruding from the holding section 17, an endoscope insertion section 21 passed through the guide pipe 18 and the holding section 17, an endoscope imaging section 22 (an imaging section) provided inside the holding section 17, a sensor 31 provided inside the holding section 17, a curve driving section 23 provided in the holding section 17, and a switch 24 (see FIG. 6) with which movement of an after-mentioned support unit 26 of the curve driving section 23 is detectable. The holding section 17 forms, for example, a cylindrical shape, and constitutes a portion (a housing) to be held with hands of a user (a surgeon). As shown in FIG. 6, the switch 24 has an abutment surface 24A that is oblique to a push direction. When the user moves the support unit 26 by use of an after-mentioned advancing/retreating mechanism 25, the abutment surface 24A of the switch 24 is pushed by the support unit 26. Consequently, the switch 24 is pushed in the push direction, and the movement of the support unit 26 is detectable. The switch 24 is one example of a detection section to detect that the endoscope 15 is projected from a distal portion 46. In the detection section to detect that the endoscope 15 is projected from the distal portion 46, an optical sensor, another sensor, another switch or the like is also usable. The sensor 31 is constituted of a gravity sensor (an acceleration sensor) which is capable of detecting a vertical direction, and a tilt of the holding section 17 (the endoscope 15 and the distal portion 46 of the guide pipe 18) to the vertical direction. The sensor 31 may be disposed in the guide pipe 18 (the distal portion 46) or in an after-mentioned distal constituting portion 27.

According to the present embodiment, as shown in FIG. 2, the endoscope 15 includes the endoscope insertion section 21 and the endoscope imaging section 22, but the endoscope 15 may integrally be a constituted of these sections. As shown in FIG. 1, it is assumed that an axial direction (a central axis direction) of an after-mentioned main body portion 44 of the guide pipe 18 is L, and in the axial direction L, an after-mentioned direction from the holding section 17 toward an elbow portion 45 is L1 and a direction from the elbow portion 45 toward the holding section 17 is L2, whereby description will be made.

The endoscope 15 is constituted of a so-called scanning type endoscope. The endoscope 15 (the endoscope insertion section 21) is flexibly constituted. Consequently, the endoscope insertion section 21 is passed through the guide pipe 18, and is therefore bendable in accordance with a shape of the guide pipe 18. An orientation of the endoscope insertion section 21 can be adjusted with the guide pipe 18. As shown in FIG. 2, in the endoscope insertion section 21, a central axis C is defined along a longitudinal direction of the section. As shown in FIG. 1, the endoscope insertion section 21 moves along a central axis C direction to be projected from the distal portion 46 of the guide pipe 18.

As shown in FIG. 2, the endoscope insertion section 21 includes the distal constituting portion 27 located on a distal side of the central axis C direction, a flexible tube 28 provided on a proximal side of the central axis C direction with respect to the distal constituting portion 27, a pair of wires (pull wires) provided on the right and the left across a distal end of a sheath 32 and the holding section 17, the tubular sheath 32 which covers the distal constituting portion 27, the flexible tube 28 and the wires, an illumination window 33. The endoscope insertion section 21 includes a rotating unit 34, an illuminating fiber 35, and receiving fibers 36. In the present embodiment, the sheath 32 is constituted to be bendable in a right-left direction (or an up-and-down direction) as shown in FIG. 1, together with the endoscope insertion section 21 (the flexible tube 28) held inside the sheath. The sensor 31 is provided in the vicinity of a distal end of the endoscope 15 (the endoscope insertion section 21). The sensor 31 is constituted of the gravity sensor (the acceleration sensor) which is capable of detecting the vertical direction, and the tilt of the vicinity of the distal end of the endoscope 15 (the endoscope insertion section 21) to the vertical direction. Consequently, the sensor 31 can detect the tilt of the vicinity of the distal end of the endoscope 15 to the vertical direction.

As shown in FIG. 1, the holding section 17 may further be provided with the advancing/retreating mechanism 25 which advances and retreats the endoscope insertion section 21 in the axial direction L through the guide pipe 18. The advancing/retreating mechanism 25 is constituted of, for example, a knob portion capable of advancing and retreating the support unit 26. That is, the user who is the surgeon can utilize the advancing/retreating mechanism 25 or the like to change a position of the endoscope insertion section 21, or can use the curve driving section 23 to change a bend angle of the endoscope insertion section 21, in a state where the endoscope insertion section 21 is inserted in a cavity (the nasal cavity, the paranasal sinus or the like) of a medical examinee in diagnosis. Consequently, a desirable image in the cavity is obtainable.

The curve driving section 23 includes the support unit 26 received in the holding section 17 to be slidable in the axial direction L of the guide pipe 18, a shaft portion 37 supported to be rotatable to the support unit 26, a dial 38 (a knob or a rotating knob) fixed to one end portion of the shaft portion 37, and an unshown sprocket fixed to the other end portion of the shaft portion 37 in a case of the support unit 26. The shaft portion 37 protrudes from a long hole 41 formed in the holding section 17 to the outside of the holding section 17. An end portion of the above wire is connected to a chain which can mesh with the sprocket. With the rotation of the dial 38, one of the above pair of wires is pulled, and the other wire loosens, whereby the distal end of the sheath 32 is pulled and the sheath 32 bends to the left or the right in FIG. 1. When the sheath 32 bends, the endoscope insertion section 21 (the flexible tube 28) which is present in the sheath also bends. A bending direction of the sheath 32 is merely one example, and the sheath 32 may bend to a distal side or a proximal side of a paper surface in FIG. 1, or needless to say, the number of the wires may be four so that the wires are bendable in four directions of the up, down, right and left directions. By pulling the wire (a linear member), the bend angle of the endoscope 15 (the endoscope insertion section 21) can be adjusted.

As shown in FIG. 2, the illuminating fiber 35 is optically connected to a light source provided adjacently to the controller 13. The light receiving fibers 36 are optically connected to an imaging element 42. Distal ends of the light receiving fibers 36 are exposed to the outside in the vicinity of the distal constituting portion 27. Consequently, with the endoscope 15, the image can be acquired via the light receiving fibers 36 in the distal constituting portion 27.

As shown in FIG. 2, the endoscope imaging section 22 includes the imaging element 42 constituted of a CCD, a CMOS, and others. The endoscope imaging section 22 can acquire the image obtained with the distal constituting portion 27 of the endoscope insertion section 21. More specifically, the imaging element 42 converts light from the light receiving fibers 36 into an electric signal to send the signal to the controller 13.

The rotating unit 34 is electrically connected to the controller 13. The rotating unit 34 is constituted of a motor and others, and is, for example, spirally swung under control of the controller 13 (a motor driver 43). Consequently, a distal end 35A of the illuminating fiber 35 is spirally swung in accordance with an operation of the rotating unit 34. Therefore, the surface of a subject is spirally scanned with illumination light from the illuminating fiber 35 through the distal end 35A of the illuminating fiber 35 and the illumination window 33. The light receiving fibers 36 receive light returned from the subject to guide the light to the imaging element 42. The imaging element 42 converts the light received by the light receiving fibers 36 into the electric signal to send the signal to the controller 13. The controller 13 converts the electric signal into the image, and suitably performs image processing to display the image in the display 14.

As shown in FIG. 1, the guide pipe 18 (a guide member) substantially forms an "L"-shape as a whole, and forms a tubular shape (a cylindrical shape) halfway bent in the form of an elbow. The guide pipe 18 includes the main body portion 44 having one end portion attached to the holding section 17, the elbow portion 45 provided in the other end portion of the main body portion 44, and the distal portion 46 protruding from the elbow portion 45 in a direction away from the main body portion 44 (i.e., in a lateral direction).

The endoscope insertion section 21 can be passed through the guide pipe 18. Along an inner wall of the guide pipe 18, the endoscope insertion section 21 which moves to advance and retreat along the central axis C can be guided. It is preferable that the guide pipe 18 is provided fixedly to, for example, the holding section 17, but may be rotatable around the axial direction L to the holding section 17. In this case, the holding section 17 may be provided with a rotating knob to rotate the guide pipe 18 around the axial direction L.

The controller 13 shown in FIG. 1 includes, for example, a controller main body 47 constituted of a usual computer, and a power source 48 provided separately from the controller main body 47. The controller main body 47 is constituted of a case 51, a circuit substrate 52 received in the case 51, a CPU, a ROM and a RAM which are mounted on the circuit substrate 52, a hard disk drive (HDD) 53, software installed in the HDD 53 to execute various types of control of the insertion device 12, the motor driver 43 received in the case 51 to control the rotating unit 34, and a mode changing button 54.

The power source 48 can supply the electric power to the rotating unit 34. The controller main body 47 can execute the control to respective sections of the insertion device 12, for example, as follows. The controller main body 47 can control the rotating unit 34 via the motor driver 43 to adjust the number of rotations and the like. The controller main body 47 can control the light source to adjust a quantity of the light to be supplied to the illuminating fiber 35. The controller main body 47 processes the electric signal corresponding to the image acquired with the imaging element 42 of the insertion device 12 to form the image, and can display the image 16 (the endoscopic image) in the display 14.

When operating the mode changing button 54, the user can sequentially change a recumbent posture first mode to perform the most suitable image rotation in observing left maxillary sinus when the medical examinee is in a recumbent posture, a recumbent posture second mode to perform the most suitable image rotation in observing right maxillary sinus when the medical examinee is in the recumbent posture, a seated posture first mode to perform the most suitable image rotation in observing the left maxillary sinus when the medical examinee is in a seated posture, and a seated posture second mode to perform the most suitable image rotation in observing the right maxillary sinus when the medical examinee is in the seated posture. In the controller main body 47, program corresponding to each of the above-mentioned modes is stored in the HDD 53.

In the program corresponding to the recumbent posture first mode, as described later, the image 16 can be rotated as much as 180 minus θ° in a counterclockwise direction around a central area of the image on predetermined conditions to be displayed in the display 14. In the program corresponding to the recumbent posture second mode, as described later, the image 16 can be rotated as much as 180 minus θ° in a clockwise direction around the central area of the image on the predetermined conditions to be displayed in the display 14. In the program corresponding to the seated posture first mode, as described later, the image 16 can be rotated as much as θ'° in the counterclockwise direction around the central area of the image on the predetermined conditions to be displayed in the display 14. In the program corresponding to the seated posture second mode, as described later, the image 16 can be rotated as much as θ'° in the clockwise direction around the central area of the image on the predetermined conditions to be displayed in the display 14.

First Example

Next, there will be described a first example of the method for observing the branch portion of the hole which uses the endoscope system of the present embodiment (the method for operating the endoscope system), with reference to FIG. 3 to FIG. 10. It is to be noted that in first to fourth examples mentioned below, it will be described that the method for observing the branch portion of the hole (the method for operating the endoscope system) is applied to the observation of the paranasal sinus (the maxillary sinus) extending laterally from the nasal cavity of the medical examinee. It is assumed that the medical examinee in the recumbent posture (in a state of lying on a bed) has left maxillary sinus observed by the user who is the surgeon. Furthermore, the observation is performed in the above-mentioned recumbent posture first mode.

Figure 7:
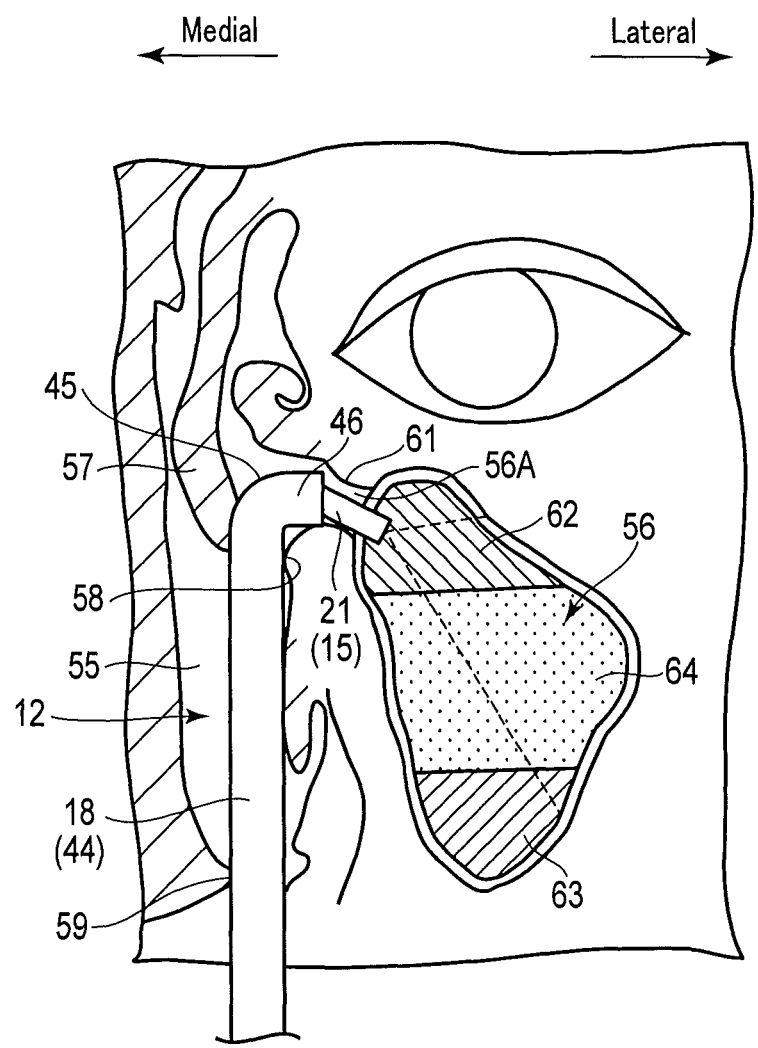
FIG. 7 is a schematic view showing a state where an endoscope and the guide pipe are inserted into a hole (the left nasal cavity) of a medical examinee in a recumbent posture and the branch portion (a paranasal sinus or the left maxillary sinus) extending laterally from a hole extending direction in a first example of a method for observing the branch portion of the hole (a method for operating the endoscope system)

As shown in FIG. 7, the maxillary sinus in the paranasal sinus constitutes a branch portion 56 extending laterally from a nasal cavity (a hole 55), the nasal cavity (the hole 55) being substantially positioned in a medial area of a face and extending in an anterior posterior direction. An area between the nasal cavity and the maxillary sinus has a middle nasal concha that is an organ dividing off this area, and a hook-shaped protrusion that is an organ dividing off the area. The hook-shaped protrusion is positioned further laterally from the middle nasal concha. When inserting the guide pipe 18 into the maxillary sinus (the branch portion 56), the user can recognize the middle nasal concha and the hook-shaped protrusion as obstacles in reaching the maxillary sinus. Consequently, in the present description, it is assumed that the middle nasal concha is conveniently an obstacle 57 and the hook-shaped protrusion is a second obstacle 61 provided before the branch portion 56 in the hole 55, whereby the description will be made. It is also assumed that the nasal cavity is the hole 55 and that the maxillary sinus is the branch portion 56, whereby the description will be made. It is to be noted that an opening 56A of the branch portion 56 (the maxillary sinus) is present at a position hidden behind the second obstacle 61 (see FIG. 5). That is, a plane (a cross section) of FIG. 7 schematically shows that the nasal cavity 55 communicates with the branch portion 56 (the maxillary sinus), but in actual, the nasal cavity 55 does not communicate with the branch portion 56 (the maxillary sinus) in the same plane (the cross section).

Figure 8:
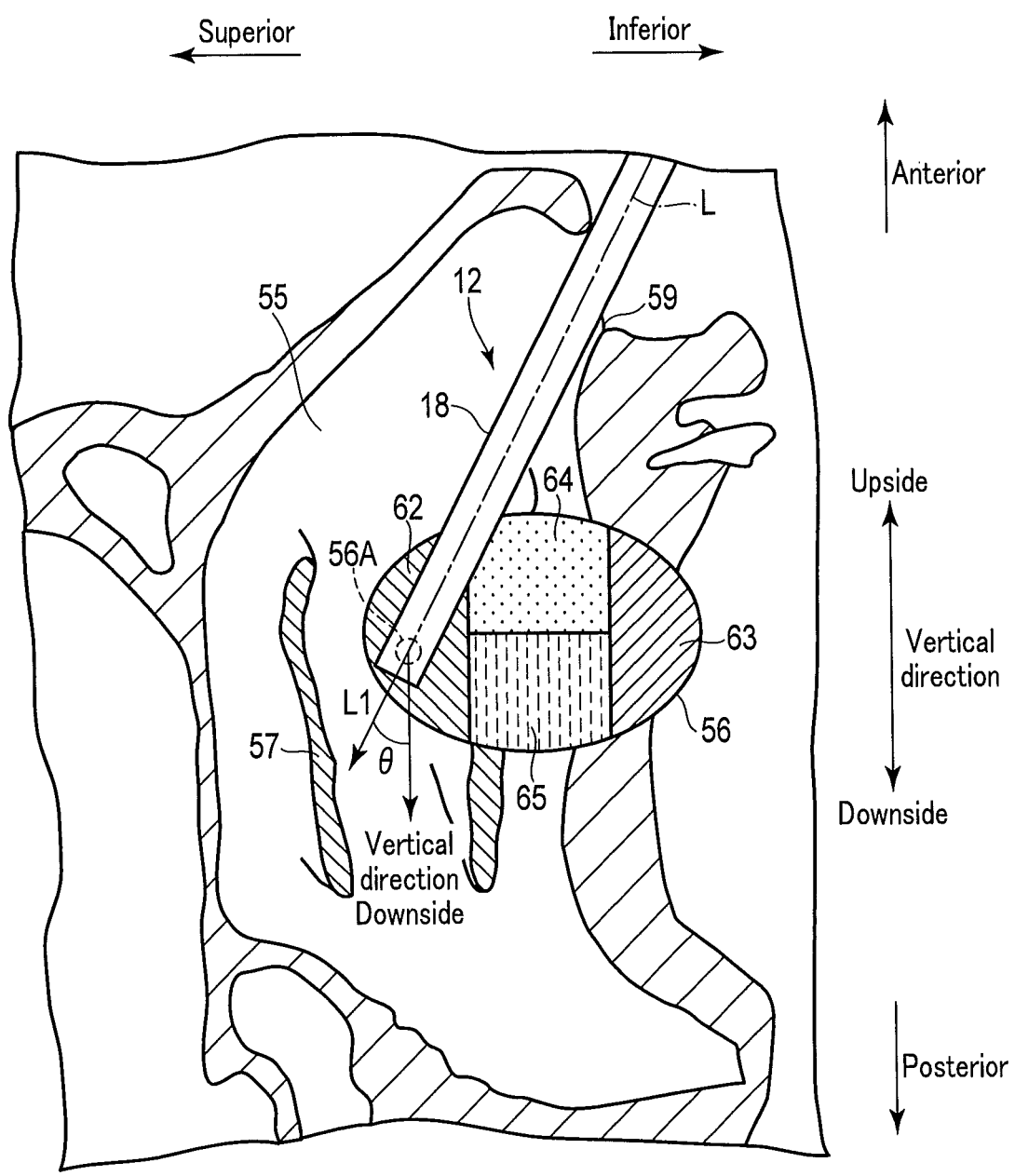
FIG. 8 is a schematic view showing the left nasal cavity shown in FIG. 7 and further showing the inside of the left maxillary sinus in a perspective manner.

As shown in FIG. 8, the user who is the surgeon can insert the guide pipe 18 into the hole 55 from an external nostril 59 of the medical examinee (the subject) in diagnosis. FIG. 8 shows a state where the guide pipe 18 is inserted in left hole 55 (a nasal cavity) of the medical examinee. As shown in FIG. 4, in the hole 55, the obstacle 57 (the middle nasal concha) is present before the branch portion 56 is reached. FIG. 4 shows an image obtained by photographing the guide pipe 18 and the obstacle 57 (the middle nasal concha) with an unshown second endoscope inserted from the external nostril 59. In the method for observing the branch portion of the hole, it is possible to observe the branch portion 56 without using such a second endoscope, but the method may be performed by use of the second endoscope which is capable of photographing such an image as shown in FIG. 4.

Figure 3:
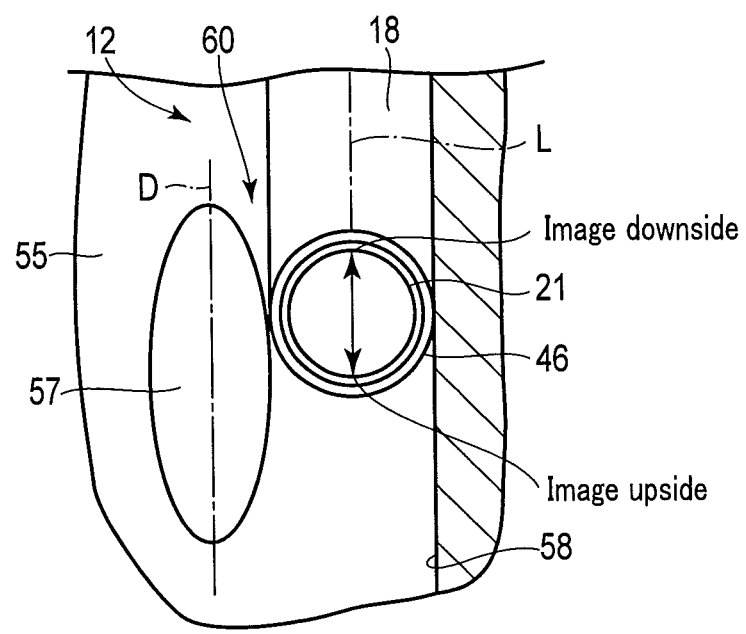
FIG. 3 is a sectional view seen from a direction opposed to a distal portion of a guide pipe, concerning positional relations of an obstacle, the guide pipe and a wall area defining a periphery of a hole.

As shown in FIG. 4, the obstacle 57 (the middle nasal concha) is located to hang down from a wall area 58 (a part of a human body) defining a periphery of the hole 55 (the nasal cavity) to a jaw (inferior) side. Here, the user can insert the guide pipe 18 into a space 60 between the wall area 58 defining the periphery of the hole 55 and the obstacle 57. Thus, the distal portion 46 of the guide pipe 18 can be advanced toward a head rear (posterior) side of the medical examinee while pushing the obstacle 57 toward the jaw (inferior) side with the elbow portion 45. At this time, the distal portion 46 of the guide pipe 18 (the distal constituting portion 27) is directed to the jaw side, and the controller 13 acquires information on an extending direction of the distal portion 46 (the distal constituting portion 27) via the sensor 31 to store the information, so that the direction of the jaw (inferior) side can be stored. As a trigger to store a jaw (inferior) side direction in the controller 13, a button operation or the like from the user is utilizable. It is preferable that the button is provided in the holding section 17 or the like. For the purpose of storing the jaw (inferior) side direction in the controller 13, the controller 13 may display whether or not "the jaw side direction is to be stored" in the display 14 after the above mode is selected with the mode changing button 54. Furthermore, as shown in FIG. 3, the longitudinal direction L of the guide pipe 18 is substantially parallel with an extending direction D of the obstacle 57. FIG. 3 is a sectional view of the guide pipe 18, the obstacle 57, and the wall area 58 defining the periphery of the hole 55 which are seen from the jaw (inferior) side.

Differently from a state of FIG. 3, the user may advance the distal portion 46 of the guide pipe 18 toward the head rear (posterior) side of the medical examinee while pushing the obstacle 57 with the distal portion 46 toward a head top (superior) side. It is to be noted that when the guide pipe 18 is advanced and retreated in a state where the distal portion 46 of the guide pipe 18 is directed to the jaw side (or the head top side), there is obtained a situation that closely resembles a state where a person walks looking downward (or upward), and hence a user's intuition is matched.

Figure 5:
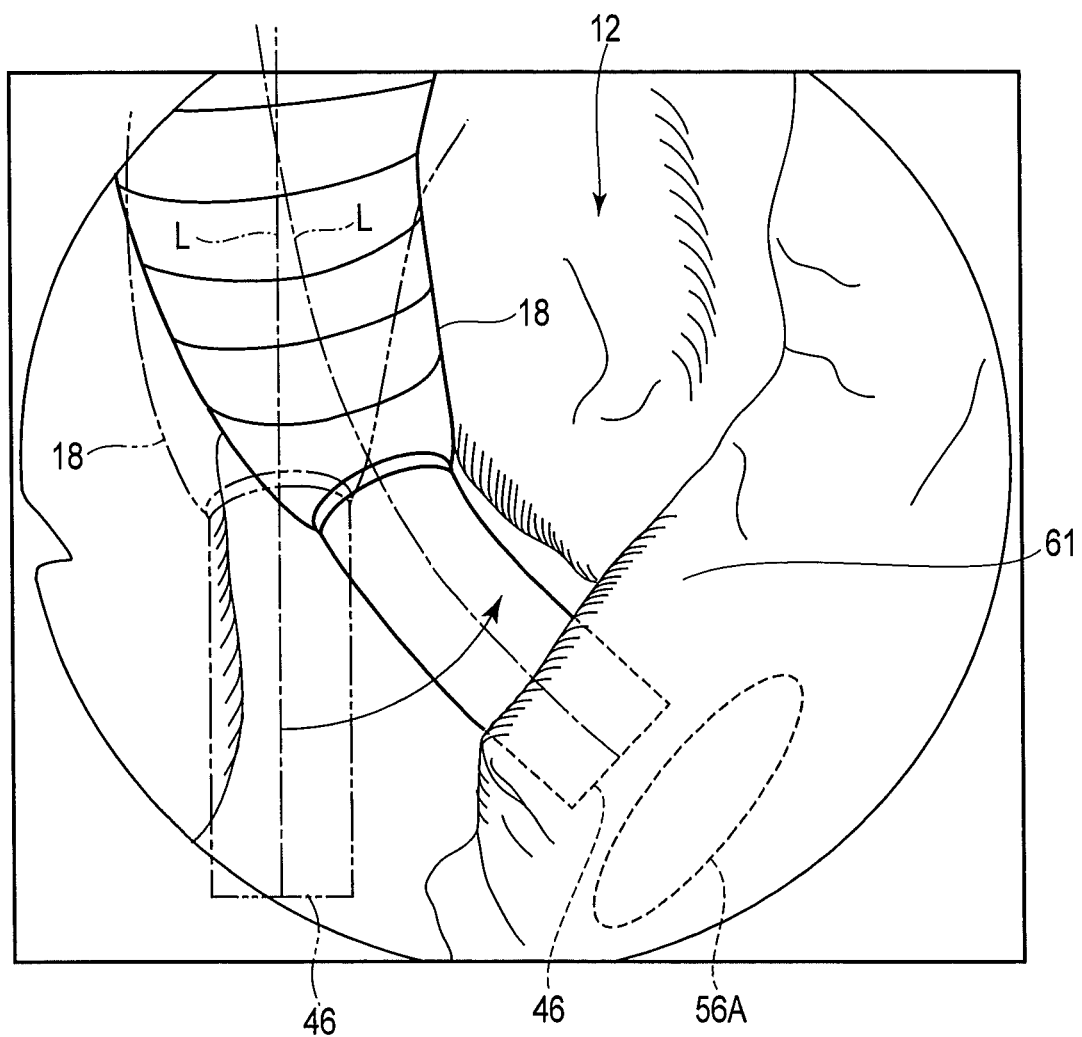
FIG. 5 is a perspective view showing, by a two-dot chain line, the guide pipe of a state prior to rotation, and showing, by a solid line (a partially broken line), a state where the guide pipe is rotated as much as 60° to 90° to raise a second obstacle (a hook-shaped protrusion) in a state where the distal portion of the guide pipe is located in the vicinity of an opening of a branch portion (a maxillary sinus)

When bringing the distal portion 46 of the guide pipe 18 closer to the opening 56A of the branch portion 56, the user twists the holding section 17 as much as about 60° to 90° around the axial direction L while pushing the obstacle 57 to the head top side with the elbow portion 45 as shown in FIG. 5, whereby the guide pipe 18 can be rotated around the axial direction L to direct the distal portion 46 laterally from the jaw side. Consequently, the distal portion 46 is laterally directed to ride over the second obstacle 61 and can be opposed to (face) the opening 56A of the branch portion 56. When the distal portion 46 of the guide pipe 18 is advanced toward the head top side, the user twists the holding section 17 as much as about 60° to 90° around the axial direction L, whereby the distal portion 46 can be opposed to the opening 56A of the branch portion 56 while the distal portion 46 is laterally directed to ride over the second obstacle 61. Thus, with the distal portion 46, the second obstacle 61 can be held in a state where the endoscope insertion section 21 (the endoscope 15) is insertable in the branch portion 56.

It is to be noted that the sensor 31 detects a degree of tilt of the vicinity of the distal end of the endoscope 15 (the distal constituting portion 27, the holding section 17 and the guide pipe 18) to the jaw (inferior) side, to always send the information to the controller main body 47. Consequently, also in circumstances where the distal portion 46 is laterally directed, the sensor 31 sends, to the controller main body 47, angular information indicating the degree of the tilt of the vicinity of the distal end of the endoscope 15 (the distal constituting portion 27, the holding section 17 and the guide pipe 18) to the jaw side. The controller main body 47 judges whether the tilt of the guide pipe 18 (the distal portion 46) to the jaw side is a threshold value (e.g., 45°) or less, or is in excess of the threshold value (e.g., 45°). The controller main body 47 stores the judgment result in the RAM or the like and holds the result until the next angular information is transmitted from the sensor 31.

In the state where the distal portion 46 of the guide pipe 18 is opposed to the opening 56A of the branch portion 56, the user utilizes the image 16 to minutely adjust the tilt of the endoscope insertion section 21 or the position of the distal constituting portion 27 as required. Furthermore, as shown in FIG. 6, the user operates the advancing/retreating mechanism 25 to push a proximal end of the endoscope insertion section 21 in the direction L1 to come close to the elbow portion 45, whereby the endoscope insertion section 21 (the endoscope 15) can be projected from the distal portion 46 of the guide pipe 18. As shown in FIG. 7, the user inserts the endoscope insertion section 21 into the opening 56A of the branch portion 56 (the maxillary sinus) while confirming the image 16 obtained from the endoscope 15.

At this time, as shown in FIG. 6, the switch 24 is pressed downward when the support unit 26 moves along the axial direction L in accordance with the movement of the advancing/retreating mechanism 25. Thus, with the switch 24, it is detected that the endoscope insertion section 21 is projected from the distal portion 46 of the guide pipe 18, to send this signal to the controller main body 47. When the controller main body 47 receives the signal indicating that the endoscope insertion section 21 is projected from the distal portion 46 of the guide pipe 18 in a state of holding the above-mentioned judgment result which is in excess of the threshold value, the image 16 displayed in the display 14 is rotated. The controller main body 47 rotates the image 16 around its central area to match the downside of the vertical direction detected by the sensor 31 with the downside of the image 16 recognized by the user and to match the upside of the vertical direction detected by the sensor 31 with the upside of the image 16 recognized by the user. For example, as shown in FIG. 8, the image 16 is rotated as much as 180 minus θ° in the counterclockwise direction at this time, in which θ° is an angle formed by the direction L1 to come close to the elbow portion 45 of the guide pipe 18 and the downside of the vertical direction. On the other hand, when the controller main body 47 receives the signal indicating that the endoscope insertion section 21 is projected from the distal portion 46 of the guide pipe 18 in the state of holding the judgment result which is not more than the above-mentioned threshold value, the rotation of the image 16 displayed in the display 14 is not performed.

At this time, a timing to rotate the image 16 by the controller main body 47 is about the same as a timing to project the endoscope insertion section 21 from the distal portion 46 of the guide pipe 18. About the same timing mentioned here is a timing of $1/10$ to $1/1000$ seconds after the controller main body 47 receives the signal indicating that the endoscope insertion section 21 is projected from the distal portion 46 of the guide pipe 18 (i.e., substantially simultaneously when the endoscope insertion section 21 is projected from the distal portion 46 of the guide pipe 18). Alternatively, about the same timing mentioned here may be a timing of several seconds after the controller main body 47 receives the signal indicating that the endoscope insertion section 21 is projected from the distal portion 46 of the guide pipe 18. Thus, it is important that the timing to rotate the image 16 is about the same as the timing to project the endoscope insertion section 21 from the distal portion 46 of the guide pipe 18. Assuming that the image 16 is rotated, for example, in advancing and retreating the guide pipe 18 in the anterior posterior direction in the nasal cavity (the hole 55), the image is displayed at an angle different from a user's intended angle, and the user might be confused. Consequently, in the present embodiment, the image 16 is rotated at the timing when the endoscope insertion section 21 is projected from the guide pipe 18 (the timing when the endoscope insertion section 21 is inserted into the opening 56A of the branch portion 56 (the maxillary sinus)), to achieve the display of the image 16 which is easy to be seen by the user.

As shown in FIG. 7 and FIG. 8, the branch portion 56 (the maxillary sinus) has a substantially triangular hollow shape (bag shape). There are individual differences in the shape of the maxillary sinus. In the present description, in the branch portion 56 (the maxillary sinus), a head top (superior) area 62, a jaw side (inferior) area 63, an anterior area 64 and a posterior area 65 are defined, whereby the description will be made. FIG. 8 shows respective areas in the branch portion 56 (the maxillary sinus) from a nasal cavity (the hole 55) side in a perspective manner.

Figure 9:
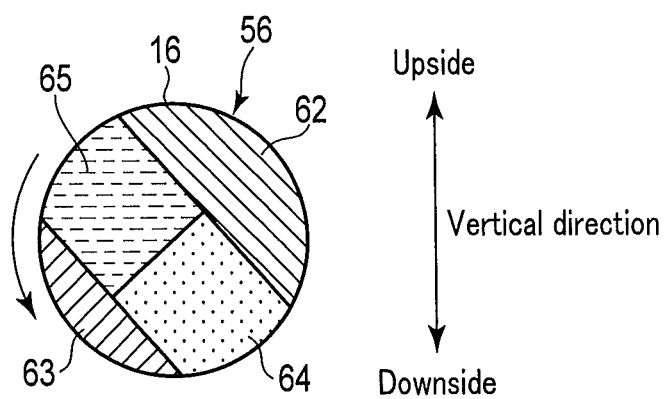
FIG. 9 is a schematic view showing an image (an image of a state prior to rotation at an angle) obtained from the endoscope in the state shown in FIG. 8.

Prior to the rotation of the image 16 by the controller main body 47, as shown in FIG. 9, the image 16 obtained from the endoscope 15 shows the head top area 62 of the branch portion 56 on an upper right side in the image 16, shows the jaw side area 63 of the branch portion 56 on a lower left side, shows the posterior area 65 of the branch portion 56 on an upper left side, and shows the anterior area 64 of the branch portion 56 on a lower right side. In this state, the user sees the medical examinee who is in the recumbent posture in front of the user, and hence the user recognizes that the upside of the image 16 (a viewing field) is the anterior area 64 of the branch portion 56 (the maxillary sinus). However, in actual, the anterior area 64 of the branch portion 56 (the maxillary sinus) is present on a lower right side in the image 16, and hence the image does not match user's sense.

Figure 10:
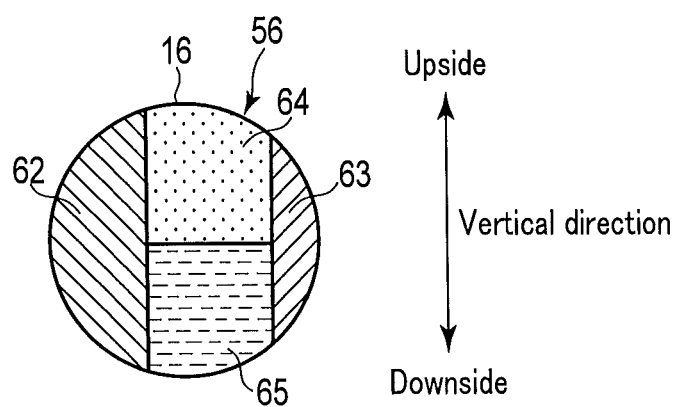
FIG. 10 is a schematic view showing an image after the image shown in FIG. 9 is rotated at the angle.

On the other hand, after the image 16 is rotated in the counterclockwise direction shown by an arrow in FIG. 9 by the controller main body 47, as shown in FIG. 10, the image shows the anterior area 64 of the branch portion 56 on the upside of the image 16, and shows the posterior area 65 of the branch portion 56 on the downside of the image 16. Furthermore, the jaw side area 63 of the branch portion 56 is shown on the right side in the image 16 and the head top area 62 of the branch portion 56 is shown on the left side in the image 16. Consequently, the upside of the image 16 recognized by the user can be matched with the upside of the vertical direction and the downside of the image 16 recognized by the user can be matched with the downside of the vertical direction. Therefore, the image 16 can be matched with the user's sense.

Thus, the user can observe the situation of the inside of the branch portion 56 (the maxillary sinus). After ending the observation of the inside of the branch portion 56, the user receives the endoscope insertion section 21 in the guide pipe 18. With the switch 24, it is detected that the endoscope insertion section 21 is received in the guide pipe 18, to send a signal corresponding to this state to the controller main body 47. The controller main body 47 cancels the above-mentioned state where the image 16 is rotated, and returns the image to its original state. The user twists the holding section 17 as much as about 60° to 90° around the axial direction L to direct the distal portion 46 of the guide pipe 18 to the jaw side (or the head top side). In this state, the user can safely remove the guide pipe 18 from the hole 55 (the nasal cavity) of the medical examinee.

Second Example

Next, there will be described a second example of the method for observing the branch portion of the hole which uses the endoscope system of the present embodiment (the method for operating the endoscope system), with reference to FIG. 11 to FIG. 14. It is assumed that a medical examinee in a recumbent posture (in a state of lying on the bed) has right maxillary sinus observed by a user who is a surgeon. Furthermore, the observation is performed in the above-mentioned recumbent posture second mode. Description of a part common with the first example is omitted.

As shown in FIG. 11, the user can insert the guide pipe 18 into a hole 55 from an external nostril 59 of the medical examinee (a subject) in diagnosis. FIG. 11 shows a state where the guide pipe 18 is inserted into right hole 55 (nasal cavity) of the medical examinee.

Similarly to the above first example, the user can insert the guide pipe 18 into a space 60 between a wall area 58 defining a periphery of the hole 55 and an obstacle 57. Thus, the user can advance a distal end of the guide pipe 18 toward a head rear (posterior) side of the medical examinee, while pushing the obstacle 57 toward a jaw side with the elbow portion 45. At this time, the controller 13 stores a direction of the jaw (inferior) side in the same manner as in the first example. Alternatively, the user may advance the distal portion 46 of the guide pipe 18 toward the head rear (posterior) side of the medical examinee, while pushing the obstacle 57 toward a head top side with the distal portion 46.

When bringing the distal portion 46 of the guide pipe 18 closer to an opening 56A of a branch portion 56, the user twists the holding section 17 as much as 60° to 90° around the axial direction L similarly to the first example shown in FIG. 5 (strictly, in a reverse direction), while pushing the obstacle 57 toward the head top side with the elbow portion 45, whereby the guide pipe 18 can be rotated around the axial direction L to direct the distal portion 46 laterally from the jaw side. Thus, the distal portion 46 is laterally directed to push a second obstacle 61 and can be opposed to (face) the opening 56A of the branch portion 56. When the distal portion 46 of the guide pipe 18 is advanced toward the head top side, the holding section 17 is twisted as much as about 60° to 90° around the axial direction L, whereby the distal portion 46 can be opposed to the opening 56A of the branch portion 56 while the laterally directed distal portion 46 rides over the second obstacle 61. Consequently, the second obstacle 61 can be held with the distal portion 46 in a state where the endoscope insertion section 21 (the endoscope 15) is insertable into the branch portion 56.

It is to be noted that the sensor 31 detects a degree of tilt of the vicinity of the distal end of the endoscope 15 to the jaw side, to always send the information to the controller main body. Consequently, also in circumstances where the distal portion 46 is laterally directed, the sensor 31 sends, to the controller main body 47, angular information indicating the degree of the tilt of the vicinity of the distal end of the endoscope 15 to the jaw side. The controller main body 47 judges whether the tilt of the guide pipe 18 (the distal portion 46) to the jaw side is a threshold value (e.g., 45°) or less, or is in excess of the threshold value (e.g., 45°). The controller main body 47 stores the judgment result in the RAM or the like and holds the result until the next angular information is transmitted from the sensor 31.

In the state where the distal portion 46 of the guide pipe 18 is opposed to the opening 56A of the branch portion 56, the user utilizes the image 16 to minutely adjust the tilt of the endoscope insertion section 21 or the position of the distal constituting portion 27 as required. The user operates the advancing/retreating mechanism 25 to project the endoscope insertion section 21 (the endoscope 15) from the distal portion 46 of the guide pipe 18, and inserts the endoscope insertion section 21 into the opening 56A of the branch portion 56 (the maxillary sinus) while confirming the image 16 obtained from the endoscope 15, as shown in FIG. 11.

Figure 12:
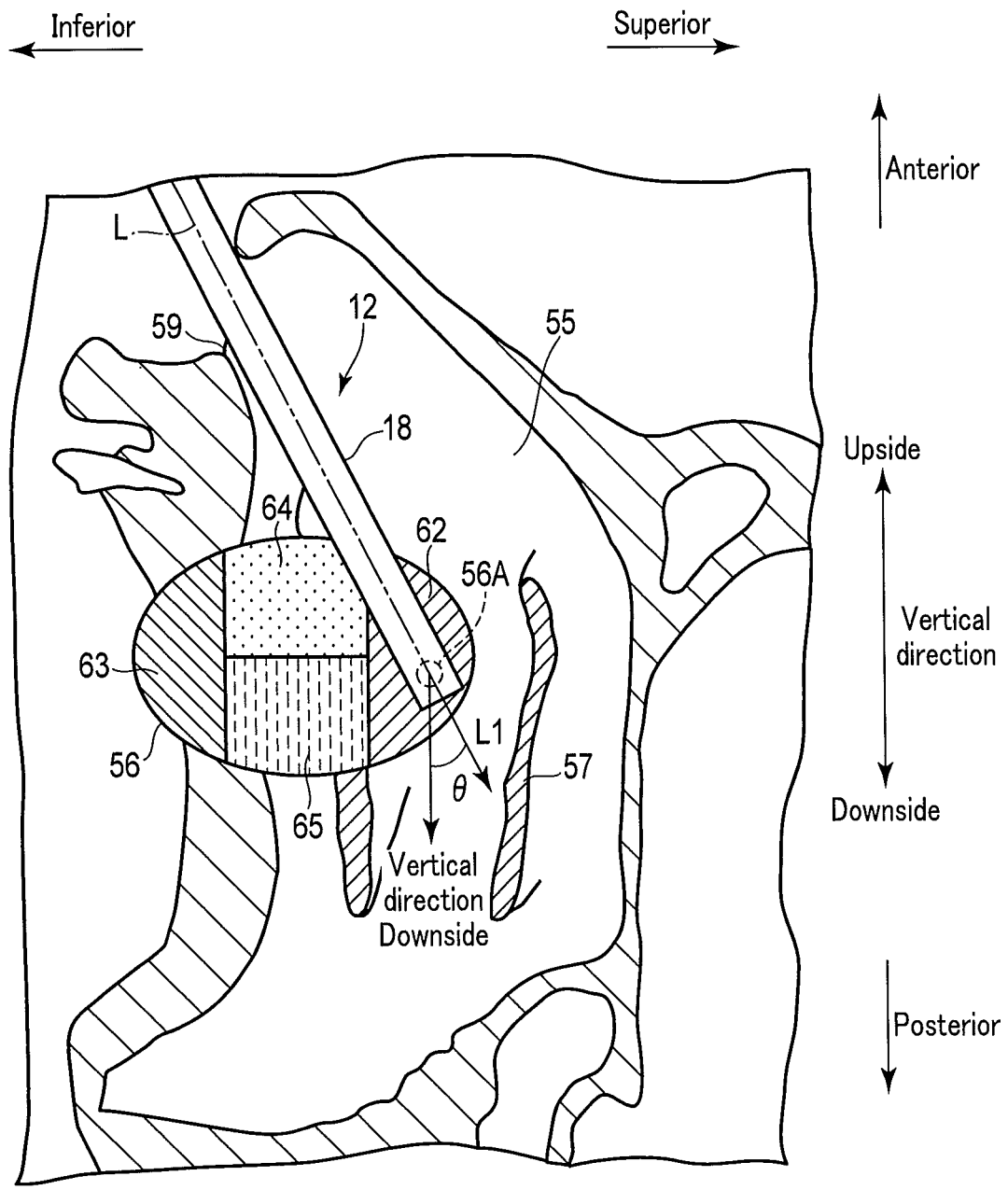
FIG. 12 is a schematic view showing the right nasal cavity shown in FIG. 11, and further showing the inside of the right maxillary sinus in a perspective manner.

At this time, as shown in FIG. 6, the switch 24 is pressed downward when the support unit 26 moves along the axial direction L in accordance with the operation of the advancing/retreating mechanism 25. Thus, with the switch 24, it is detected that the endoscope insertion section 21 is projected from the distal portion 46 of the guide pipe 18, to send this signal to the controller main body 47. When the controller main body 47 receives the signal indicating that the endoscope insertion section 21 is projected from the distal portion 46 of the guide pipe 18 in a state of holding the above-mentioned judgment result which is in excess of the threshold value, the image 16 displayed in the display 14 is rotated. The controller main body 47 rotates the image 16 around its central area to match the downside of the vertical direction detected by the sensor 31 with the downside of the image 16 recognized by the user and to match the upside of the vertical direction detected by the sensor 31 with the upside of the image 16 recognized by the user. For example, as shown in FIG. 12, the image 16 is rotated as much as 180 minus θ° in the clockwise direction at this time, in which θ° is an angle formed by the direction L1 to come close to the elbow portion 45 of the guide pipe 18 and the downside of the vertical direction. On the other hand, when the controller main body 47 receives the signal indicating that the endoscope insertion section 21 is projected from the distal portion 46 of the guide pipe 18 in the state of holding the judgment result which is not more than the above-mentioned threshold value, the rotation of the image 16 displayed in the display 14 is not performed.

At this time, a timing to rotate the image 16 by the controller main body 47 is about the same as a timing to project the endoscope insertion section 21 from the distal portion 46 of the guide pipe 18. About the same timing mentioned here is a timing of 1/10 to 1/1000 seconds after the controller main body 47 receives the signal indicating that the endoscope insertion section 21 is projected from the distal portion 46 of the guide pipe 18 (i.e., substantially simultaneously when the endoscope insertion section 21 is projected from the distal portion 46 of the guide pipe 18). Alternatively, about the same timing mentioned here may be a timing of several seconds after the controller main body 47 receives the signal indicating that the endoscope insertion section 21 is projected from the distal portion 46 of the guide pipe 18.

FIG. 11 shows respective areas in the branch portion 56 (the maxillary sinus) from the side of the nasal cavity (the hole 55) in a perspective manner. Prior to the rotation of the image 16 by the controller main body 47, as shown in FIG. 13, the image 16 obtained from the endoscope 15 shows a head top area 62 of the branch portion 56 on an upper left side in the image 16, shows a jaw side area 63 of the branch portion 56 on a lower right side, shows a posterior area 65 of the branch portion 56 on an upper right side, and shows an anterior area 64 of the branch portion 56 on a lower left side. In this state, the user sees the medical examinee who is in the recumbent posture in front of the user, and hence the user recognizes that the upside of the image 16 (a viewing field) is the anterior area 64 of the branch portion 56 (the maxillary sinus). However, in actual, the anterior area 64 of the branch portion 56 (the maxillary sinus) is present on a lower left side in the image 16, and hence the image does not match user's sense.

On the other hand, after the image 16 is rotated in a clockwise direction shown by an arrow in FIG. 13 by the controller main body 47, as shown in FIG. 14, the image shows the anterior area 64 of the branch portion 56 on the upside of the image 16, and shows the posterior area 65 of the branch portion 56 on the downside of the image 16. Furthermore, the jaw side area 63 of the branch portion 56 is shown on the left side of the image 16 and the head top area 62 of the branch portion 56 is shown on the right side of the image 16. Consequently, the upside of the image 16 recognized by the user can be matched with the upside of the vertical direction and the downside of the image 16 recognized by the user can be matched with the downside of the vertical direction. Therefore, the rotated image 16 can be matched with the user's sense.

Thus, the user can observe the situation of the inside of the branch portion 56 (the maxillary sinus). After ending the observation of the inside of the branch portion 56, the user receives the endoscope insertion section 21 in the guide pipe 18. With the switch 24, it is detected that the endoscope insertion section 21 is received in the guide pipe 18, to send a signal corresponding to this state to the controller main body 47. The controller main body 47 cancels the above-mentioned state where the image 16 is rotated, and returns the image to its original state. The user twists the holding section 17 as much as about 60° to 90° to direct the distal portion 46 of the guide pipe 18 to the jaw side (or the head top side). In this state, the user can safely remove the guide pipe 18 from the hole 55 (the nasal cavity) of the medical examinee.

Third Example

Next, there will be described a third example of the method for observing the branch portion of the hole which uses the endoscope system 11 of the present embodiment (the method for operating the endoscope system), with reference to FIG. 15 to FIG. 18. It is assumed that a medical examinee in a seated posture (a sitting state) has left maxillary sinus observed by a user who is a surgeon. Furthermore, the observation is performed in the above-mentioned seated posture first mode. Description of a part common with the first example is omitted.

Figure 15:
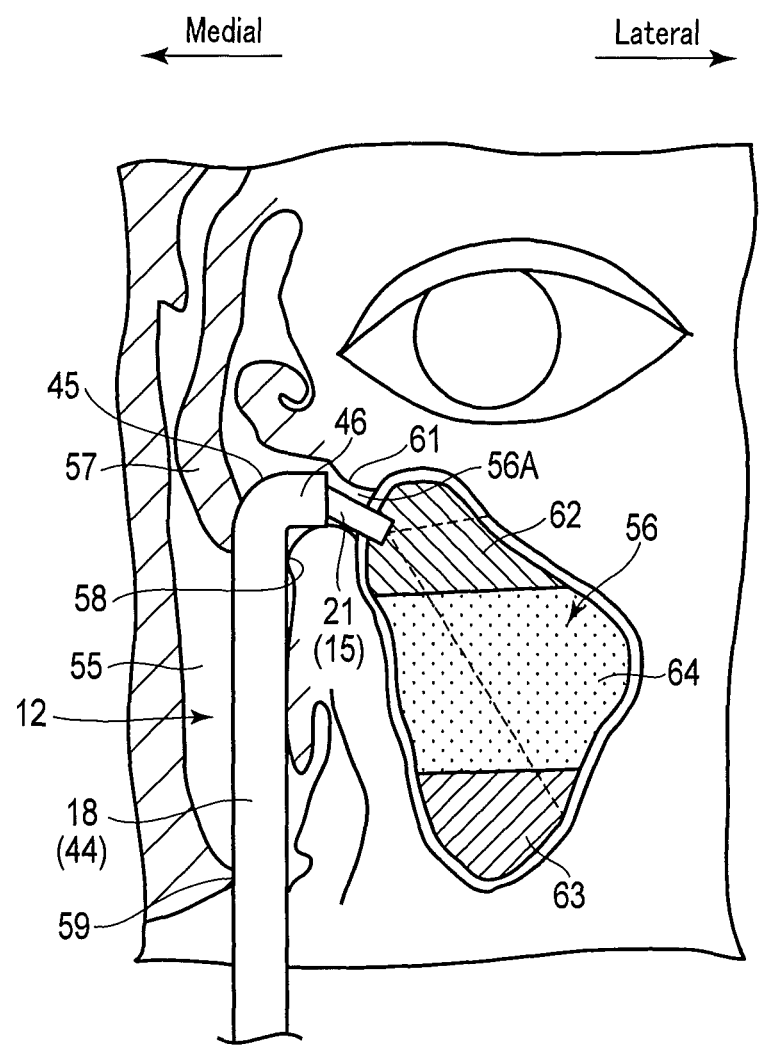
FIG. 15 is a schematic view showing a state where the endoscope and the guide pipe are inserted into a hole (left nasal cavity) of a medical examinee in a seated posture and a branch portion (a paranasal sinus or left maxillary sinus) in a third example of the method for observing the branch portion of the hole (the method for operating the endoscope system)

As shown in FIG. 15, the user can insert the guide pipe 18 into a hole 55 from an external nostril 59 of the medical examinee (a subject) in diagnosis. FIG. 15 shows a state where the guide pipe 18 is inserted in left hole 55 (nasal cavity) of the medical examinee.

The user performs a procedure similar to the first example so that the distal portion of the guide pipe 18 can be opposed to (face) an opening 56A of a branch portion 56. That is, the user can advance the distal portion 46 of the guide pipe 18 toward a head rear (posterior) side of the medical examinee in a hole 55 (nasal cavity), while pushing an obstacle 57 toward the downside or upside of a vertical direction with the elbow portion 45. In this state, the user utilizes the image 16 to minutely adjust the tilt of the endoscope insertion section 21 or the position of the distal constituting portion 27 as required. The user operates the advancing/retreating mechanism 25 to project the endoscope insertion section 21 (the endoscope 15) from the distal portion 46 of the guide pipe 18, and inserts the endoscope insertion section 21 into the opening 56A of the branch portion 56 (the maxillary sinus) while confirming the image 16 obtained from the endoscope 15, as shown in FIG. 15. The sensor 31 detects a degree of tilt of the vicinity of the distal end of the endoscope 15 to the downside of the vertical direction, to always send the information to the controller main body. Consequently, also in circumstances where the distal portion 46 is laterally directed, the sensor 31 sends, to the controller main body 47, angular information indicating the degree of the tilt of the vicinity of the distal end of the endoscope 15 to the downside of the vertical direction. The controller main body 47 judges whether the tilt of the guide pipe 18 (the distal portion 46) to the downside of the vertical direction is a threshold value (e.g., 45°) or less, or is in excess of the threshold value (e.g., 45°). The controller main body 47 stores the judgment result in the RAM or the like and holds the result until the next angular information is transmitted from the sensor 31.

Figure 16:
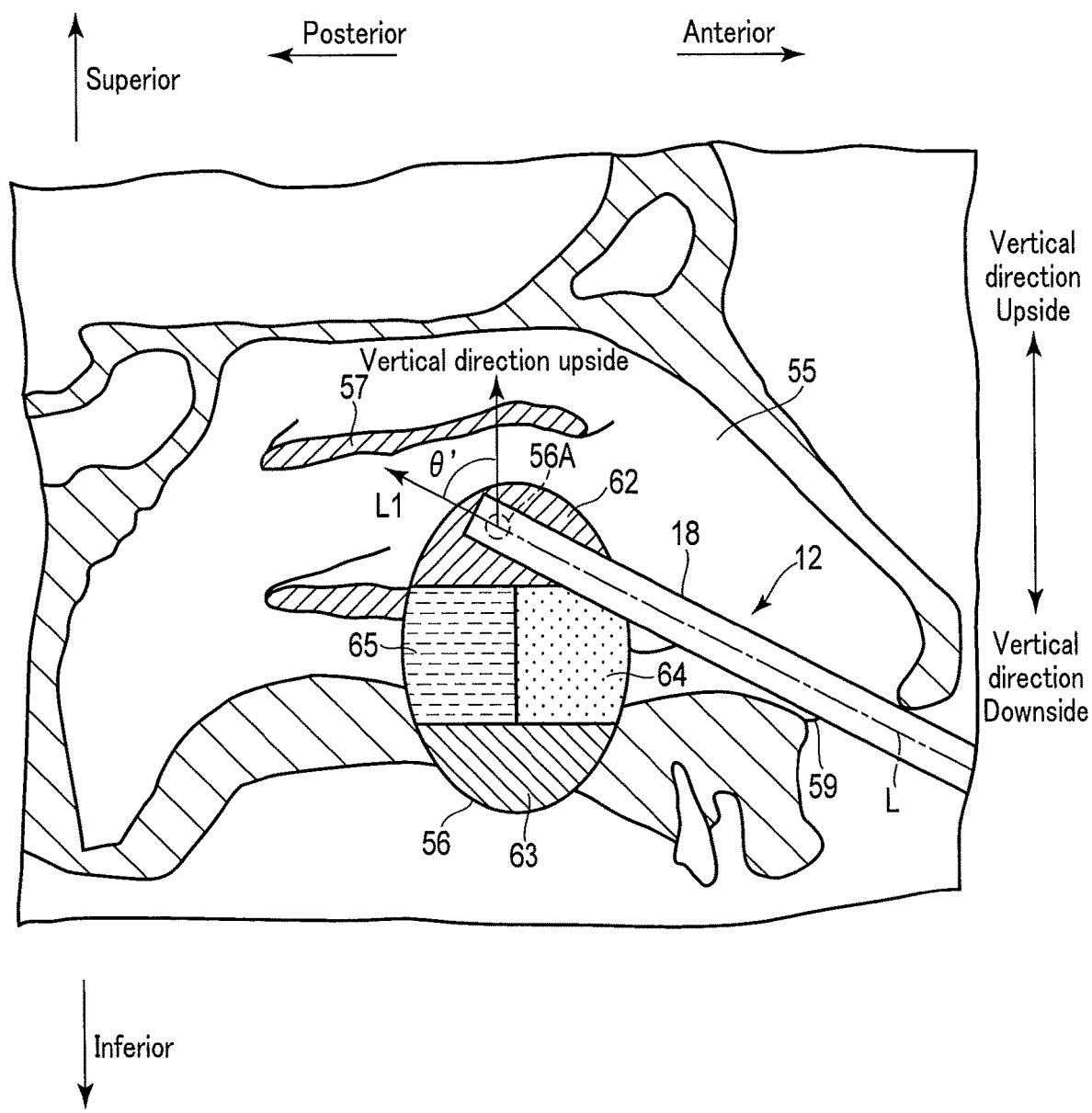
FIG. 16 is a schematic view showing the left nasal cavity shown in FIG. 15, and further showing the inside of the left maxillary sinus in a perspective manner.

At this time, as shown in FIG. 6, the switch 24 is pressed downward when the support unit 26 moves along the axial direction L in accordance with the operation of the advancing/retreating mechanism 25. Thus, with the switch 24, it is detected that the endoscope insertion section 21 is projected from the distal portion 46 of the guide pipe 18, to send this signal to the controller main body 47. When the controller main body 47 receives the signal indicating that the endoscope insertion section 21 is projected from the distal portion 46 of the guide pipe 18 in a state of holding the above-mentioned judgment result which is in excess of the threshold value, the image 16 displayed in the display 14 is rotated. The controller main body 47 rotates the image 16 around its central area to match the downside of the vertical direction detected by the sensor 31 with the downside of the image 16 recognized by the user and to match the upside of the vertical direction detected by the sensor 31 with the upside of the image 16 recognized by the user. For example, as shown in FIG. 16, the image 16 is rotated as much as $\theta'°$ in a counterclockwise direction at this time, in which $\theta'°$ is an angle formed by the upside direction of the vertical direction and the direction L1 which comes close to the elbow portion 45 of the guide pipe 18. On the other hand, when the controller main body 47 receives the signal indicating that the endoscope insertion section 21 is projected from the distal portion 46 of the guide pipe 18 in the state of holding the judgment result which is not more than the above-mentioned threshold value, the rotation of the image 16 displayed in the display 14 is not performed.

FIG. 16 shows respective areas in the branch portion 56 (the maxillary sinus) from the side of the nasal cavity in a perspective manner. Prior to the rotation of the image 16 by the controller main body 47, as shown in FIG. 17, the image 16 obtained from the endoscope 15 shows a head top area 62 of the branch portion 56 on an upper right side in the image, shows a jaw side area 63 of the branch portion 56 on a lower left side, shows a posterior area 65 of the branch portion 56 on an upper left side, and shows an anterior area 64 of the branch portion 56 on a lower right side. In this state, the user sees the medical examinee who is in the seated posture in front of the user, and hence the user recognizes that the upside of the image 16 (a viewing field) is the head top area 62 of the branch portion 56 (the maxillary sinus). However, in actual, the head top area 62 of the branch portion 56 (the maxillary sinus) is present on an upper right side in the image 16, and hence the image does not match user's sense.

On the other hand, after the image 16 is rotated in a counterclockwise direction shown by an arrow in FIG. 17 by the controller main body 47, as shown in FIG. 18, the image 16 shows the head top area 62 of the branch portion 56 on the upside of the image, and shows the jaw side area 63 of the branch portion 56 on the downside of the image 16. Furthermore, the anterior area 64 of the branch portion 56 is shown on the right side in the image 16 and the posterior area 65 of the branch portion 56 is shown on the left side in the image 16. Consequently, the upside of the image 16 recognized by the user can be matched with the upside of the vertical direction and the downside of the image 16 recognized by the user can be matched with the downside of the vertical direction. Therefore, the image 16 can be matched with the user's sense.

Thus, the user can observe the situation of the inside of the branch portion 56 (the maxillary sinus). After ending the observation of the inside of the branch portion 56, the user receives the endoscope insertion section 21 in the guide pipe 18. With the switch 24, it is detected that the endoscope insertion section 21 is received in the guide pipe 18, to send a signal corresponding to this state to the controller main body 47. The controller main body 47 cancels the above-mentioned state where the image 16 is rotated, and returns the image to its original state. The user twists the holding section 17 as much as about 60° to 90° to direct the distal portion 46 of the guide pipe 18 to the downside of the vertical direction (or the upside of the vertical direction). In this state, the user can safely remove the guide pipe 18 from the hole 55 (the nasal cavity) of the medical examinee.

Fourth Example

Next, there will be described a fourth example of the method for observing the branch portion of the hole which uses the endoscope system 11 of the present embodiment (the method for operating the endoscope system). Similarly, to the above third example, a user who is a surgeon can observe right maxillary sinus of a medical examinee in a seated posture (a sitting state). Furthermore, this observation is performed in the above-mentioned seated posture second mode. Description of a part common with the third example is omitted.

The user performs a procedure similar to the second example so that the distal portion 46 of the guide pipe 18 can be opposed to (face) an opening of a branch portion 56. That is, the user can advance the distal portion 46 of the guide pipe 18 toward a head rear (posterior) side of the medical examinee in a hole 55 (nasal cavity), while pushing an obstacle 57 toward the downside or upside of a vertical direction with the elbow portion 45. In this state, the user utilizes the image 16 obtained from the endoscope 15 to minutely adjust the tilt of the endoscope insertion section 21 or the position of the distal constituting portion 27 as required. The user operates the advancing/retreating mechanism 25 to project the endoscope insertion section 21 (the endoscope 15) from the distal portion 46 of the guide pipe 18, and inserts the endoscope insertion section 21 into an opening 56A of the branch portion 56 (the maxillary sinus) while confirming the image 16 obtained from the endoscope 15.

At this time, as shown in FIG. 6, the switch 24 is pressed downward when the support unit 26 moves along the axial direction L in accordance with the operation of the advancing/retreating mechanism 25. Thus, with the switch 24, it is detected that the endoscope insertion section 21 is projected from the distal portion 46 of the guide pipe 18, to send this signal to the controller main body 47. When the controller main body 47 receives the signal indicating that the endoscope insertion section 21 is projected from the distal portion 46 of the guide pipe 18 in a state of holding the above-mentioned judgment result which is in excess of the threshold value in the same manner as in the first example, the image 16 displayed in the display 14 is rotated. The controller main body 47 rotates the image 16 around its central area to match the downside of the vertical direction detected by the sensor 31 with the downside of the image 16 recognized by the user and to match the upside of the vertical direction detected by the sensor 31 with the upside of the image 16 recognized by the user. For example, the image 16 is rotated as much as θ'° in a clockwise direction at this time, in which θ'° is an angle formed by the upside direction of the vertical direction and the direction L1 which comes close to the elbow portion 45 of the guide pipe 18. On the other hand, when the controller main body 47 receives the signal indicating that the endoscope insertion section 21 is projected from the distal portion 46 of the guide pipe 18 in the state of holding the judgment result which is not more than the above-mentioned threshold value, the rotation of the image 16 displayed in the display 14 is not performed.

In a state prior to the rotation, in actual, a head top side of the branch portion 56 (the maxillary sinus) is present on an upper left side in the image 16, and hence the image does not match user's sense. After the image 16 is rotated in the clockwise direction by the controller main body 47, the image 16 shows a head top area 62 of the branch portion 56 on the upside of the image, and shows a jaw side area 63 of the branch portion 56 on the downside of the image 16. Furthermore, an anterior area 64 of the branch portion 56 is shown on the left side in the image 16 and a posterior area 65 of the branch portion 56 is shown on the right side in the image 16. Consequently, the image 16 can be matched with the user's sense.

According to the embodiments, conclusion can be made as follows. That is, a method for observing a branch portion of a hole uses an endoscope system 11 including a guide member having an elbow portion 45 and a distal portion 46 extending laterally from the elbow portion 45, an endoscope 15 whose orientation is adjustable by the guide member, a controller 13 which processes a signal acquired from the endoscope 15 to generate an image 16, and a display 14 which displays the image 16 generated by the controller 13. The method for observing the branch portion of the hole includes a step of pushing an obstacle 57 in a hole 55 with the elbow portion 45, a step of rotating the guide member around an axial direction L so that the distal portion 46 faces a branch portion 56 extending laterally to an extending direction of the hole 55, a step of projecting the endoscope 15 from the distal portion 46 and inserting into the branch portion 56 while confirming the image 16, and a step of rotating the image 16 to match an up-and-down direction of the image 16 recognized by a user with an up-and-down of a vertical direction after the endoscope 15 is inserted into the branch portion 56.

Usually, when the branch portion 56 extending laterally from the extending direction of the hole 55 is observed, it is necessary to noticeably bend the endoscope 15 and guide the endoscope to an observation area by use of the guide member having the elbow portion 45, or the like. In this case, the endoscope 15 is bent, and hence the user is apt to lose a sense of direction. According to the above constitution, the up-and-down direction of the image 16 recognized by a user can be matched with the up-and-down of the vertical direction, and hence the image 16 can be displayed to match the user's sense. Consequently, during the observation, the user can efficiently perform the observation without losing the sense of direction. Furthermore, time required for the observation can be shortened. This method is remarkably useful especially for observation of an area which does not have any landmarks, e.g., a maxillary sinus of a human body, because the user does not lose the sense of direction.

In this case, the endoscope system 11 includes a sensor 31 provided in the vicinity of a distal end of the endoscope 15 to detect tilt of the vicinity of the distal end of the endoscope 15 to the vertical direction, and a detection section to detect that the endoscope 15 is projected from the distal portion 46, and in the step of rotating the image 16, the controller 13 rotates the image 16 to match the up-and-down direction of the image 16 recognized by the user with the up-and-down of the vertical direction at about the same timing as a timing when it is detected by the detection section that the endoscope 15 is projected from the distal portion 46.

According to this constitution, substantially simultaneously when the endoscope 15 reaches the inside of the branch portion 56, the image 16 can be rotated to match user's sense. Consequently, the user can efficiently observe the inside of the branch portion 56 under an environment which is intuitively recognizable.

The hole 55 and the branch portion 56 are the hole 55 and branch portion 56 of a medical examinee, and when the medical examinee is in a recumbent posture, in the step of rotating the image 16, the upside of the image 16 recognized by the user is an anterior side of the medical examinee, and when the medical examinee is in a seated posture, in the step of rotating the image 16, the upside of the image 16 recognized by the user is a head top side of the medical examinee.

A structure in the human body corresponding to the upside of the image 16 recognized by the user when the medical examinee is in the recumbent posture is different from that when the medical examinee is in the seated posture. According to the present embodiment, whether the posture of the medical examinee is the recumbent posture or the seated posture, the image 16 can be rotated in a direction which is easy to be recognized by the user. Consequently, the user can efficiently observe the inside of the hole 55.

The hole 55 is a nasal cavity, the branch portion 56 is the maxillary sinus extending laterally to the extending direction of the nasal cavity, and the obstacle 57 is middle nasal concha. According to this constitution, the method for observing the branch portion of the hole is applicable to the maxillary sinus of the human body. Consequently, the maxillary sinus can efficiently be observed, and the user does not lose the sense of direction during the observation of the maxillary sinus. Consequently, there does not occur the disadvantage that the endoscope 15 moves in an unintended direction and that the endoscope 15 comes in contact with an inner wall of the maxillary sinus.

According to the above embodiment, the endoscope system 11 includes a guide member having an elbow portion 45 and a distal portion 46 extending laterally from the elbow portion 45, an endoscope 15 whose orientation is adjustable by the guide member, a controller 13 which processes a signal acquired from the endoscope 15 to generate an image 16, and a display 14 which displays the image 16 generated by the controller 13. A method for operating the endoscope system includes a step of rotating the guide member around an axial direction L so that the distal portion 46 faces a branch portion 56 extending laterally to an extending direction of a hole 55, a step in which the controller 13 receives a signal indicating that the endoscope 15 is inserted in the branch portion 56, and a step in which the controller 13 rotates the image 16 to match an up-and-down direction of the image 16 recognized by a user with an up-and-down of a vertical direction after the signal is received.

According to this constitution, after the endoscope 15 is inserted into the branch portion 56, it is possible to immediately match the upside of the image 16 recognized by the user with the upside of the vertical direction and to immediately match the downside of the image 16 recognized by the user with the downside of the vertical direction. When the laterally extending branch portion 56 is observed, the user is apt to lose a sense of direction, but according to the constitution, the user does not lose the sense of direction, and it is possible to achieve the method for operating the endoscope system which enables efficient observation. This method is remarkably useful especially for observation of an area which does not have any landmarks, e.g., a maxillary sinus of a human body, because the user does not lose the sense of direction.

In this case, the endoscope system 11 includes a sensor 31 provided in the vicinity of a distal end of the endoscope 15 to detect tilt of the vicinity of the distal end of the endoscope 15 to the vertical direction, and a detection section to detect that the endoscope 15 is projected from the distal portion 46, and the method for operating the endoscope system includes a step in which the detection section detecting that the endoscope 15 is projected from the distal portion 46 sends the signal to the controller 13, after the step of rotating the guide member around the axial direction L.

According to this constitution, it is possible to easily achieve a structure to send, to the controller 13, the signal indicating that the endoscope 15 is inserted in the branch portion 56.

It is to be noted that in the present embodiment, with the switch 24, it is detected that the endoscope insertion section 21 is projected from the distal portion 46 of the guide pipe 18, but the switch 24 may be replaced with a push button (a switch) provided in the holding section 17 or the controller main body 47. The user can push the push button at an optional timing. When this constitution is employed, the user operates the push button at a timing to rotate the image 16 (e.g., a timing when the endoscope 15 reaches the branch portion 56 (the maxillary sinus)), whereby the image 16 can be rotated as in the above first to fourth example. A direction and an angle in rotating the image 16 are similar to those of the above first to fourth examples. Furthermore, an observation mode such as a recumbent posture first mode is set in the same manner as in the above first to fourth examples.

(Modification)

Figure 19:
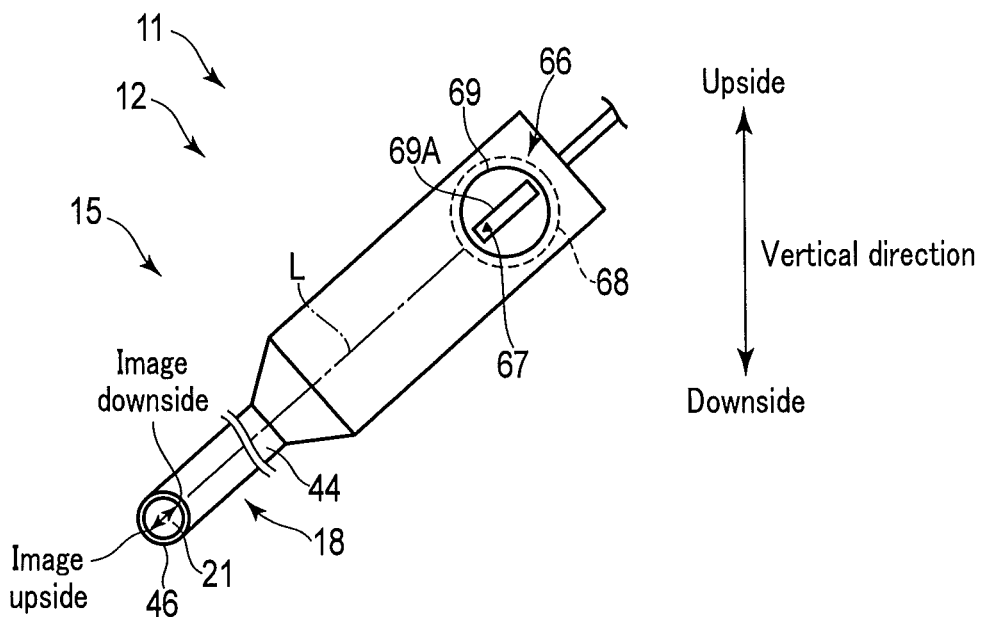
FIG. 19 is a schematic view schematically showing an entire configuration of an insertion device of an endoscope system according to a first modification and an up-and-down direction of an image recognized by a user.
Figure 20:
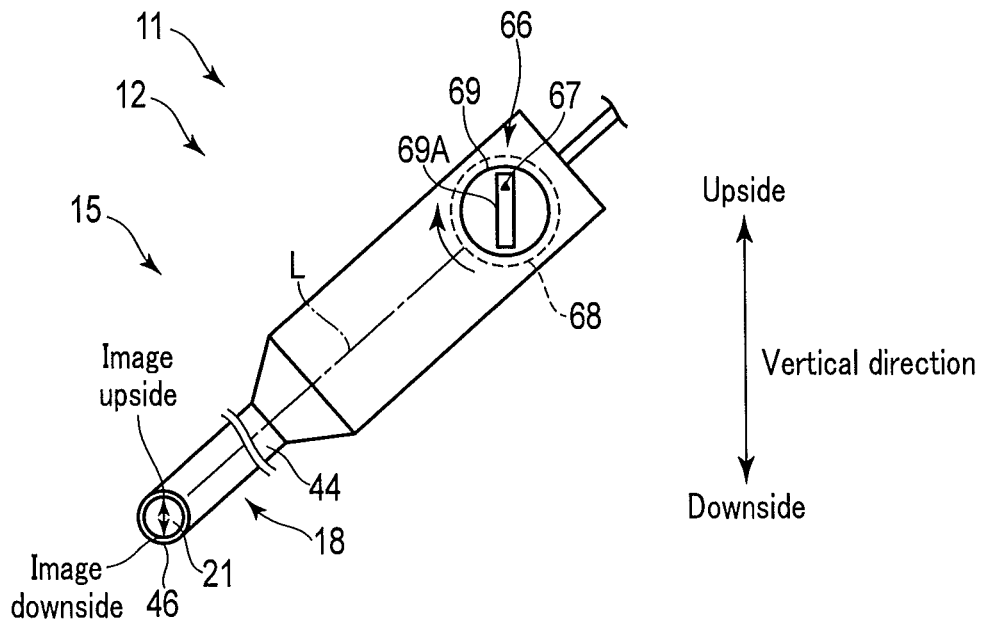
FIG. 20 is a schematic view schematically showing a state where the up-and-down direction of the image recognized by the user are matched with an up-and-down of a vertical direction in the insertion device shown in FIG. 19.

Next, there will be described an endoscope system 11 of a modification and a method for observing a branch portion of a hole which uses the endoscope system (a method for operating the endoscope system), with reference to FIG. 19 and FIG. 20. Here, a part different from the above embodiment is mainly described, and drawing and description of a part common with the above embodiment are omitted. In the present modification, a user can manually change an up-and-down direction of an image 16 to a direction which is easy to be seen.

In a holding section 17 of an insertion device 12, there is provided an operation section 66 to rotate the image 16 displayed in a display 14 at an optional angle. The operation section 66 includes an operation dial 69 constituted to be turnable to the holding section 17, a protrusion piece 69A provided to protrude from a flat surface of the operation dial 69, a triangular index 67 provided on a top surface of the protrusion piece 69A, and a potentiometer 68 which is included in the holding section under the operation dial 69 and which detects a turning amount (a turning angle) of the operation dial 69 and sends a signal corresponding to the amount to a controller main body 47. The index 67 corresponds to, for example, the upside of the image 16 (a screen) displayed in the display 14.

An HDD 53 of the controller main body 47 stores program. According to this program, the image 16 is rotated around its central area as much as the same rotation amount (rotation angle) as the turning amount (the turning angle) of the operation dial 69 in the same direction as a turning direction of the operation dial 69, on the basis of the signal corresponding to the turning amount (the turning angle) of the operation dial 69 which is sent from the potentiometer 68. Consequently, according to the program, when the user turns the operation dial 69, the controller main body 47 rotates the image 16 as much as the same rotation amount as the turning amount of the operation dial 69 from an initial position in the same direction as the turning direction of the operation dial 69 to display the image in the display 14.

Next, there will be described the method for observing the branch portion of the hole which uses the endoscope system 11 of the present modification (the method for operating the endoscope system), with reference to FIG. 19 and FIG. 20. Here, it is described that the method for observing the branch portion of the hole is applied to observation of a paranasal sinus (a maxillary sinus) extending laterally from a nasal cavity of a medical examinee. It is assumed that the medical examinee in a recumbent posture (in a state of lying on the bed) has left maxillary sinus observed by the user who is a surgeon. Furthermore, the observation is performed in the above-mentioned recumbent posture first mode.

As shown in FIG. 8, the user who is the surgeon can insert a guide pipe 18 into a hole 55 from an external nostril 59 of the medical examinee (a subject) in diagnosis. The user then performs a technique similar to a first example of the above embodiment so that a distal portion 46 of the guide pipe 18 can be opposed to (face) an opening 56A of a branch portion 56. In this state, the user utilizes the image 16 obtained from an endoscope 15 to minutely adjust tilt of an endoscope insertion section 21 and a position of a distal constituting portion 27 as required. The user operates an advancing/retreating mechanism 25 to project the endoscope insertion section 21 (the endoscope 15) from the distal portion 46 of the guide pipe 18, and inserts the endoscope insertion section 21 into the opening 56A of the branch portion 56 (the maxillary sinus) while confirming the image 16 obtained from the endoscope 15.

The user can rotate the operation section 66 to rotate the image 16 displayed in the display 14 at a timing when the vicinity of a distal end of the endoscope insertion section 21 reaches the branch portion 56 (the maxillary sinus), a timing of elapse of predetermined time after the branch portion 56 (the maxillary sinus) is reached, or a timing before reaching the branch portion 56 (the maxillary sinus).

The user sees the medical examinee in the recumbent posture in front of the user, and hence the upside of the image 16 recognized by the user corresponds to an anterior side of the branch portion 56 (the maxillary sinus). As shown in FIG. 19, in a state prior to the rotation of the image 16, the upside of the image 16 ((an anterior area 64 of the branch portion 56) recognized by the user is displayed on a lower left side in the display 14, and the downside of the image 16 (a posterior area 65 of the branch portion 56) recognized by the user is displayed on an upper right side in the display 14. In this state, the image 16 displayed in the display 14 does not match user's sense, and has a state which is hard to be seen by the user.

When the user turns the operation dial 69 of the operation section 66 to change an orientation indicated by the index 67 to the upside of a vertical direction, the potentiometer 68 detects the turning angle of the operation dial 69 from its initial position to send the signal corresponding to the angle to the controller main body 47. On the basis of the signal, the controller main body 47 rotates the image 16 around its central area in the same direction as the turning direction of the operation dial 69 and rotates the image 16 as much as the same angle as the turning angle of the operation dial 69. Consequently, the upside of the image 16 recognized by the user (the anterior side of the branch portion 56) can be matched with the upside of the vertical direction, and the downside of the image 16 recognized by the user (the downside of the branch portion 56) can similarly be matched with the downside of the vertical direction.

Thus, the user can observe a situation of the inside of the branch portion 56 (the maxillary sinus). After ending the observation of the inside of the branch portion 56, the user receives the endoscope insertion section 21 in the guide pipe 18. The user can return the operation section 66 to its initial position to return the angle of the image 16 to the angle prior to the rotation, at a timing when the endoscope insertion section 21 is received or at a much later timing. The user further twists the holding section 17 as much as about 60° to 90° to direct the distal portion 46 of the guide pipe 18 to a jaw side (or a head top side). In this state, the user can safely remove the guide pipe 18 from the hole 55 (the nasal cavity) of the medical examinee.

It is to be noted that in the present modification, the index 67 corresponds to the upside of the image 16 (the screen) displayed in the display 14, but the index 67 may correspond to the downside of the image 16 (the screen) displayed in the display 14.

According to the present modification, the endoscope system 11 includes the operation section 66, and in the method for observing the branch portion of the hole, in a step of rotating the image 16, the user operates the operation section 66 to rotate the image 16 so that the up-and-down direction of the image 16 recognized by the user matches with the up-and-down of the vertical direction. According to this constitution, the user can manually adjust the angle of the image 16 displayed in the display 14. Consequently, the user can observe the inside of the branch portion 56 at an angle at which the inside is easy to be seen, and can efficiently perform the observation.

The operation section 66 is rotatably constituted, and in the method for observing the branch portion of the hole, in the step of rotating the image 16, the user rotates the operation section 66 so that the image 16 is adjustable at an optional angle. According to this constitution, the rotation of the operation section 66 corresponds to the rotation of the image 16, and hence the user can intuitively perform a rotating operation of the image 16. Consequently, it is possible to achieve a user-friendly method for observing the branch portion of the hole, and it is possible to improve efficiency of the observation so that observation time can be decreased.

According to the present modification, the endoscope system 11 includes the operation section 66 to be operated by the user, and the method for operating the endoscope system further includes a step in which the operation section 66 operated by the user sends the signal to a controller 13 after a step of rotating the guide member around an axial direction L. According to this constitution, the user who sees the image 16 judges that the endoscope 15 is inserted in the branch portion 56, and the user operates the operation section 66 so that the controller 13 can receive a signal indicating that the endoscope 15 is inserted in the branch portion 56. Consequently, the controller 13 can borrow user's sense of vision to easily grasp that the endoscope 15 enters the branch portion 56. Consequently, a wrong operation of rotating the image 16 at a user's unintended timing is hard to occur, and it is possible to achieve a user-friendly method for operating the endoscope system.

Hitherto, the embodiment and the respective modifications have specifically be described with reference to the drawings, but this invention is not limited to the above-mentioned embodiment, and constituent elements can be modified and embodied without departing from the gist of the invention. In the above embodiment, a scanning type endoscope is used, but needless to say, in the method for observing the branch portion of the hole and the method for operating the system, a non-scanning type endoscope (a so-called usual endoscope) which does not have the rotating unit 34 is also usable. In the above embodiment and the respective modifications, there has been described the observation of the maxillary sinus in the paranasal sinus, but needless to say, the above-mentioned method for observing the paranasal sinus is also applicable to observation of a frontal sinus or an ethmoidal sinus in the paranasal sinus. Furthermore, needless to say, the method for observing the branch portion of the hole and the method for operating the endoscope system are usable not only in inspection and observation of the human body but also in observation of the inside of a branch portion 56 of a hole 55 (a pipe or a duct) in a mechanical structure. Furthermore, the above embodiment may be combined with the above modification to achieve one endoscope system, the method for observing the branch portion of the hole or the method for operating the endoscope system.

Furthermore, in the above embodiment and the respective modifications, an observation target is the paranasal sinus, but the above-mentioned observing method is also applicable to a sinus or a canal in the human body, e.g., urinary bladder which has less landmarks in the same manner as in the paranasal sinus.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method for observing a maxillary sinus which uses an endoscope system comprising a guide member having an elbow and a distal portion extending laterally from the elbow, an endoscope inserted through the guide member, a controller which processes a signal acquired from the endoscope to generate an image, a display which displays the image generated by the controller, and a switch which detects that the endoscope is projected from the distal portion by reacting to an advancing movement of the endoscope, the method for observing the maxillary sinus comprising:
    inserting the guide member from an external nostril to a nasal cavity;
    pushing a middle nasal concha of the nasal cavity with the elbow portion;
    rotating the guide member around an axis of a portion on a proximal end side of the guide member relative to the elbow so that the distal portion faces the maxillary sinus extending laterally to an extending direction of the nasal cavity in a state where the middle nasal concha is pushed;
    projecting the endoscope from the distal portion to insert the endoscope into the maxillary sinus, while confirming the image;
    detecting an insertion of the endoscope into the maxillary sinus based on the advancing movement detected by the switch; and
    subsequent to the projecting, rotating the image to match an up-and-down direction of the image with a predetermined up-and-down direction.

2. The method for observing the maxillary sinus according to claim 1,
    further comprising detecting that the endoscope is projected from the distal portion,
    wherein the rotating of the image comprises rotating the image to match the up-and-down direction of the image with the predetermined up-and-down-direction at about a same timing as a timing when detecting that the endoscope is projected from the distal portion.

3. The method for observing the maxillary sinus according to claim 1, wherein
    the endoscope system further comprises an operation section, and
    the rotating of the image comprises the user operating the operation section to rotate the image to match the up-and-down direction of the image with the predetermined up-and-down direction.

4. The method for observing the maxillary sinus according to claim 3, wherein
    the operation section is rotatable around an axis of the operation section, and
    the rotating of the image comprises the user rotating the operation section around the axis of the operation section so that the image is adjustable at an optional angle.

5. The method for observing the maxillary sinus according to claim 1, wherein
    the nasal cavity and the maxillary sinus are a nasal cavity and a maxillary sinus of a medical examinee,
    when the medical examinee is in a recumbent posture, in the rotating of the image, the upside of the predetermined up-and-down direction is an anterior side of the medical examinee, and
    when the medical examinee is in a seated posture, in the rotating of the image, the upside of the predetermined up-and-down direction-is a head top side of the medical examinee.

6. A method for operating an endoscope system comprising a guide member having an elbow and a distal portion extending laterally from the elbow, an endoscope inserted through the guide member, a controller which processes a signal acquired from the endoscope to generate an image, a display which displays the image generated by the controller, and a switch which detects that the endoscope is projected from the distal portion by reacting to an advancing movement of the endoscope, the method for operating the endoscope system comprising:
    rotating the guide member inserted from an external nostril into a nasal cavity around an axis of a portion on a proximal end side of the guide member relative to the elbow so that the distal portion faces a maxillary sinus extending laterally to an extending direction of a hole;
    projecting the endoscope into the maxillary sinus;
    detecting, by the switch, the projection of the endoscope into the maxillary sinus;
    outputting, to the controller, a signal from the switch indicating that the endoscope is inserted into the maxillary sinus;
    receiving a signal at the controller indicating that the endoscope is inserted in the maxillary sinus; and
    subsequent to the receiving, rotating the image at the controller to match an up-and-down direction of the image with a predetermined up-and-down.

7. The method for operating the endoscope system according to claim 6, wherein
    the endoscope system further comprises an operation section to be operated by the user,
    subsequent to the rotating of the guide member, the receiving comprises, receiving the signal from the operation section.

8. The method for operating the endoscope system according to claim 6, wherein
the nasal cavity and the maxillary sinus-are a nasal cavity and a maxillary sinus of a medical examinee,
when the medical examinee is in a recumbent posture, in the rotating of the image, the upside of the predetermined up-and-down direction is an anterior side of the medical examinee, and
when the medical examinee is in a seated posture, in the rotating of the image, the upside of the predetermined up-and-down direction is a head top side of the medical examinee.

9. The method of operating the endoscope system according to claim 6, further comprising generating the image based on the signal from the endoscope;
wherein the outputting of the signal from the switch is performed independently from the generating of the image.

10. The method of operating the endoscope system according to claim 6, wherein, the detecting by the switch comprises pressing the switch.

11. A method for operating an endoscope system comprising a guide member having an elbow and a distal portion extending laterally from the elbow, an endoscope inserted through the guide member, a controller which processes a signal acquired from the endoscope to generate an image, and a display which displays the image generated by the controller, the method for operating the endoscope system comprising:
rotating the guide member inserted from an external nostril into a nasal cavity around an axis of a portion on a proximal end side of the guide member relative to the elbow so that the distal portion faces a maxillary sinus extending laterally to an extending direction of a hole;
receiving a signal at the controller indicating that the endoscope is inserted in the maxillary sinus; and
subsequent to the receiving, rotating the image at the controller to match an up-and-down direction of the image with a predetermined up-and-down;
wherein
the endoscope system further comprises:
a sensor provided in the vicinity of a distal end of the endoscope to detect tilt of the vicinity of the distal end of the endoscope relative to a vertical direction; and
a switch to detect that the endoscope is projected from the distal portion,
the method for operating the endoscope system further comprising detecting by the switch, that the endoscope is projected from the distal portion; and
the receiving comprises sending the signal, from the switch, to the controller, after the rotating of the guide member around the axis.

* * * * *